United States Patent
Zhou et al.

(10) Patent No.: US 6,284,783 B1
(45) Date of Patent: Sep. 4, 2001

(54) USE OF BISINDOLYLMALEIMIDE COMPOUNDS TO INDUCE FAS-MEDIATED APOPTOSIS

(75) Inventors: Tong Zhou, Hoover; Richard Scott Jope, Vestavia, both of AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/328,707

(22) Filed: Jun. 9, 1999

(51) Int. Cl.$^7$ .............................. A01N 43/38; A61K 31/40
(52) U.S. Cl. ............................................................ 514/414
(58) Field of Search ............................................ 514/414

(56) References Cited

U.S. PATENT DOCUMENTS

| | | | |
|---|---|---|---|
| 4,923,986 | 5/1990 | Murakata et al. | 540/545 |
| 4,935,415 | 6/1990 | Nakano et al. | 514/211 |
| 5,015,578 | 5/1991 | Schroeder et al. | 435/119 |
| 5,057,614 | 10/1991 | Davis et al. | 548/466 |
| 5,260,294 | 11/1993 | Walser | 514/230.5 |
| 5,264,431 | 11/1993 | Wacker et al. | 514/211 |
| 5,292,747 | 3/1994 | Davis et al. | 514/285 |
| 5,344,926 | 9/1994 | Murakata et al. | 540/545 |
| 5,380,746 | 1/1995 | Barth et al. | 514/414 |
| 5,399,712 | 3/1995 | Hill | 578/455 |
| 5,405,864 | 4/1995 | Broka | 514/415 |
| 5,438,050 | 8/1995 | Kleinschroth et al. | 514/183 |
| 5,455,241 | 10/1995 | Wacker | 514/211 |
| 5,481,003 | 1/1996 | Gillig et al. | 548/455 |
| 5,491,242 | 2/1996 | Gillig et al. | 548/455 |
| 5,545,636 | 8/1996 | Heath, Jr. et al. | 514/214 |
| 5,552,396 | 9/1996 | Heath, Jr. et al. | 514/183 |

(List continued on next page.)

OTHER PUBLICATIONS

Bit et al., "Inhibitors of Protein Kinase C. 3. Potent and Highly Selective Bisindolylmaleimides by Conformational Restriction", J. Med. Chem. 36, pp. 21–29, 1993.*

Abstract to Guo et al, "Inhibition of the expresion of mitogen–activated protein phosphatase–1 potentiates apoptosis induced by tumor necrosis factor–alpha in rat mesangial cells", J. Biol. Chem. 273(17), pp. 10362–10366, 1998.*

Alessi et al., (1997) The protein kinase C inhibitors Ro 318220 and GF 109203X are equally potent inhibitors . . . FEBS Lett., 402:121–123.

Beltman et al. (1999) C3 toxin activates the stress signaling pathways, JNK and p38, but antagonizes . . . J. Biol. Chem., 274:3772–3780.

Beltman et al. (1996) The selective protein kinase C inhibitor, Ro–31–8220, inhibits mitogen–activated protein . . . J. Biol. Chem., 271:27018–27024.

Berge et al. (1977) Pharmaceutical salts. J. Pharm. Sci., 66:1–19.

Bit et al. (1993) Inhibitors of protein kinase C. 3. Potent and highly selective bisindolylmaleimides by conformational restriction. J. Med. Chem., 36:21–29.

Brunner et al. (1995) Cell–autonomous Fas (CD95)/fas–ligand interaction mediates activation–induced apoptosis in T–cell hybridomas. Nature, 373:441–444.

Chang et al., (1990) Dissecting Fas signaling with an altered–specificity death–domain mutant: requirement of FADD binding for apoptosis but not Jun N–terminal kinase activation. Proc. Natl. Acad. Sci, USA, 96:1252–1256.

Chatenoud (1998) Tolerogenic antibodies and fusion proteins to prevent graft rejection and treat autoimunity. Mol. Med. Today, 4:25–30.

Dhein et al. (1995) Autocrine T–cell suicide mediated by APO–1/(Fas/CD95). Nature, 373:438–441.

Ehl et al. (1996) Different susceptibility of cytotoxic T cells to CD95 (Fas/Apo–1) ligand–mediated cell death after activation in vitro versus in vivo. J. Immunol., 156:2357–2360.

Itoh et al. (1991) The polypeptide encoded by the cDNA for human cell surface antigen Fas can mediate apoptosis. Cell, 66:233–243.

(List continued on next page.)

Primary Examiner—Dwayne C. Jones
(74) Attorney, Agent, or Firm—Gifford, Krass, Groh, Sprinkle, Anderson & Citkowski, P.C.

(57) ABSTRACT

The present invention provides a method of inducing apoptosis in target cells of a subject by administering, to the subject a pharmaceutically effective amount of at least one compound of the formula:

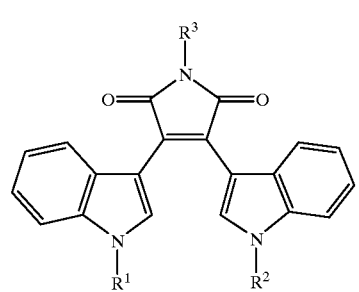

I wherein:
  $R^1$ is hydrogen, $C_1$–$C_{12}$ alkyl, $C_1$–$C_{12}$ substituted alkyl, $C_3$–$C_7$ heterocycle, or $C_3$–$C_7$ substituted heterocycle, $R^2$ and $R^3$ are independently H or $C_1$–$C_{12}$ alkyl, and the pharmaceutically acceptable salts, esters, amides, and prodrugs thereof, wherein following the administration of the compound of Formula I, the target cell is caused to undergo apoptosis.

30 Claims, 12 Drawing Sheets

U.S. PATENT DOCUMENTS

| | | | |
|---|---|---|---|
| 5,661,173 | 8/1997 | Heath, Jr. et al. | 514/414 |
| 5,672,618 | 9/1997 | Heath, Jr. et al. | 514/414 |
| 5,710,145 | 1/1998 | Engel et al. | 514/183 |
| 5,821,072 | 10/1998 | Schwartz et al. | 435/15 |
| 5,821,365 | 10/1998 | Jirousek et al. | 540/469 |
| 6,103,713 | 8/2000 | Ways et al. | 514/183 |

OTHER PUBLICATIONS

Jacobson et al. (1997) Programmed cell death in animal development Cell, 88:347–354.

Jacobson et al. (1995) Anti–inflammatory properties of Go 6850: a selective inhibitor of protein kinase C. J. Pharmacol. Exp. Therap., 275:995–1002.

Ju et al. (1995) Fas(CD95)/fast interactions required for programmed cell death after T–cell activation. Nature, 373:444–448.

Miyawaki et al. (1992) Differential expression of apoptosis–related Fas antigen on lymphocyte subpopulations in human peripheral blood. J. Immunol., 149:3753–3758.

Nagata (1997) Apoptosis by death factor. Cell, 88:355–365.

Saas et al. (1997) Fas ligand expression by astrocytoma in vivo: maintaining immune privilege in the Brain? J. Clin. Invest., 99:1173–1178.

Su et al. (1995) Defective expression of hematopoietic cell protein tyrosine phosphatase (HCP) in lymphoid cells blood Fas–mediated apoptosis. Immunity, 2:353–362.

Suda et al., (1993) Molecular cloning and expression of the Fas ligand, a novel member of the tumor necrosis factor family. Cell, 75:1178.

Suen et al. (1997) A critical role of lymphotoxin in experimental allergic encephalomyelitis. J. Exp. Med., 186:1233–1240.

Sun et al. (1988) Suppression of experimentally induced autoimmune encephalomyelitis by cytolytic T–T cell interactions. Nature, 332:843–845.

Suschek et al. (1999) Nitric oxide fully protects against UVA–induced apoptosis in tight correlation with Bcl–2 up–regulation. J. Biol. Chem., 274:6130–6137.

Tabi et al. (1995) Antigen–specific down–regulation of myelin basic protein–reactive T cells during spontaneous recovery from experimental autoimmune encephalomyelitis: further evidence of apoptotic deletion . . . Int. Immunol., 7:967–973.

Takahashi et al. (1994) Generalized lymphoproliferative disease in mice, caused by a point mutation in the Fas ligand. Cell, 76:969–976.

Watanabe–Fukunaga et al. (1992) Lymphoproliferation disorder in mice explained by defects in Fas antigen that mediates apoptosis. Nature, 356:314–317.

Weller et al. (1994) Anti–Fas/APO–1 antibody–mediated apoptosis of cultured human glioma cells. Induction and modulation of sensitivity by cytokines. J. Clin. Invest., 94:954–964.

Yeo et al. (1997) Dissociation of tyrosine phosphorylation and activation of phosphoinositide phospholipase C induced by the protein kinase C inhibitor Ro–31–8220 in Swiss 3T3 cells treated with platelet–derived growth factor. Biochim. Biophys. Acta, 1356:308–320.

Yonehara et al. (1989) A cell–killing monoclonal antibody (Anti–Fas) to a cell surface antigen co–downregulated with the receptor of tumor necrosis factor. J. Exp. Med., 169:1747–1756.

Zhou et al. (1999) Bisindolylmaleimide VIII facilites Fas–mediated apoptosis and inhibits T cell–mediated autoimmune diseases. Nature Medicine, 5:42–48.

* cited by examiner

Figure 2a
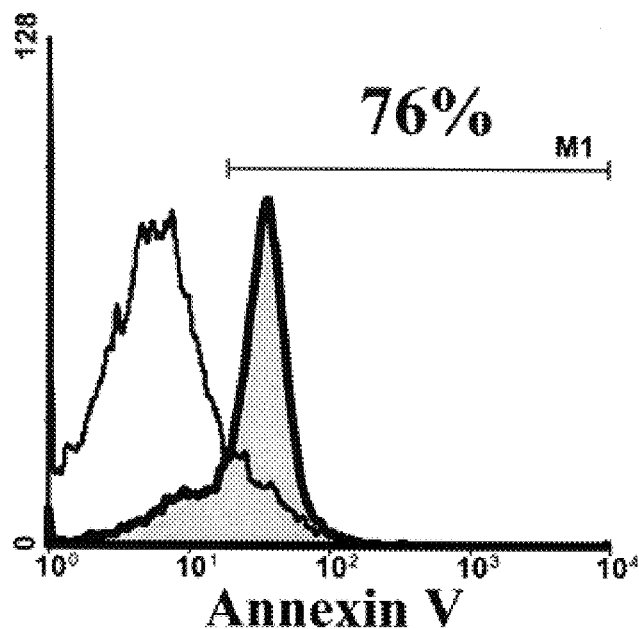
Figure 2b
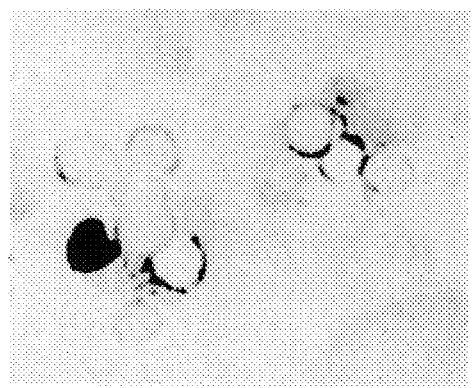
Anti-Fas
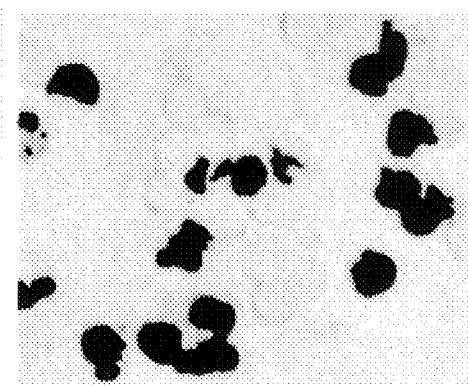
Anti-Fas + BISVIII
Figure 2c

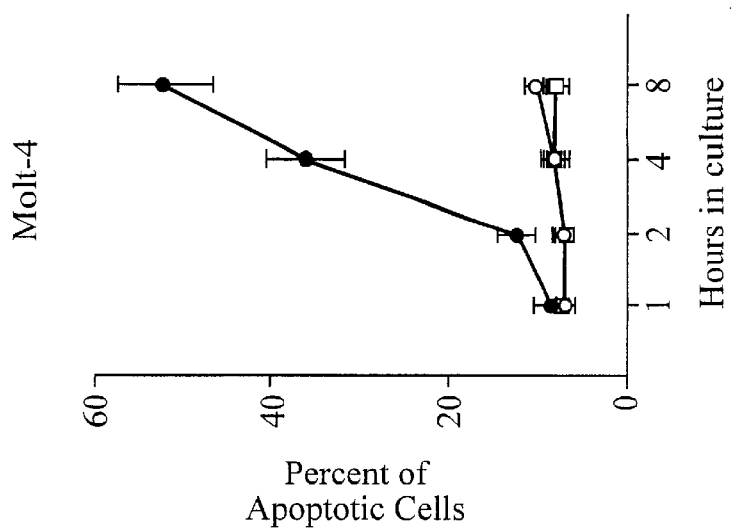
Fig - 5c Molt-4
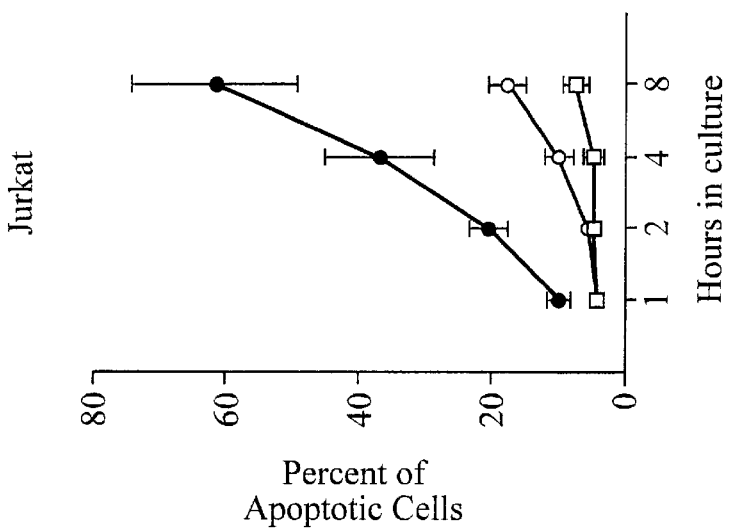
Fig - 5b Jurkat
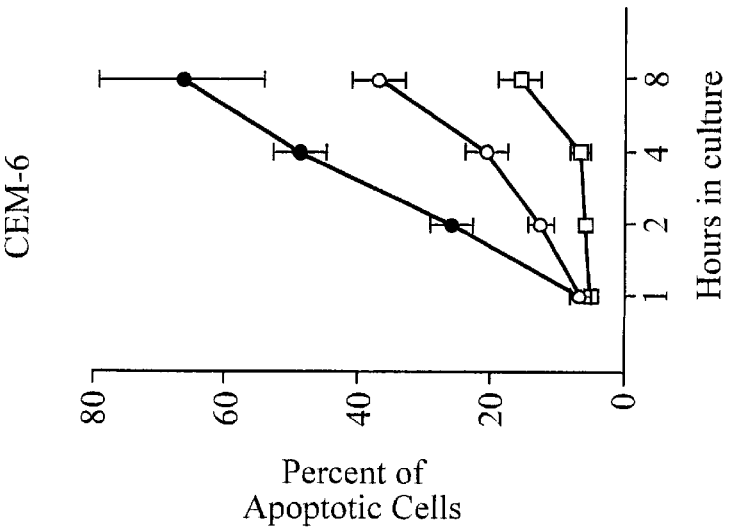
Fig - 5a CEM-6

(A) Membrane fraction
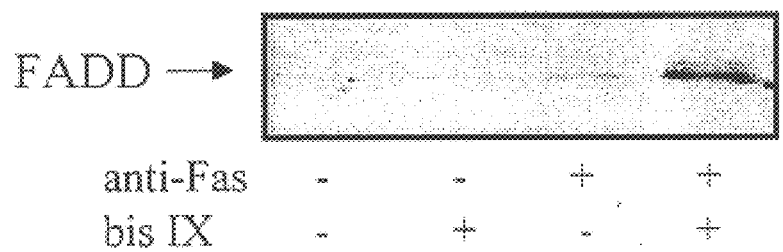
(B) Co-immunoprecipitation
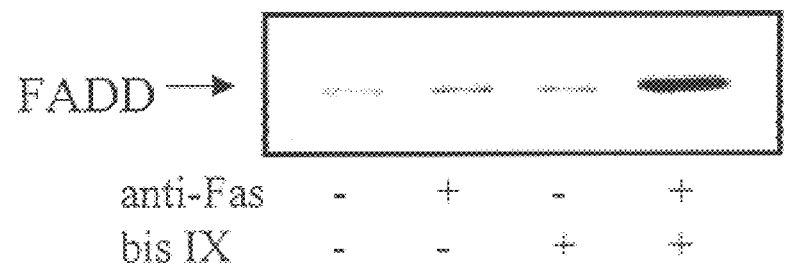
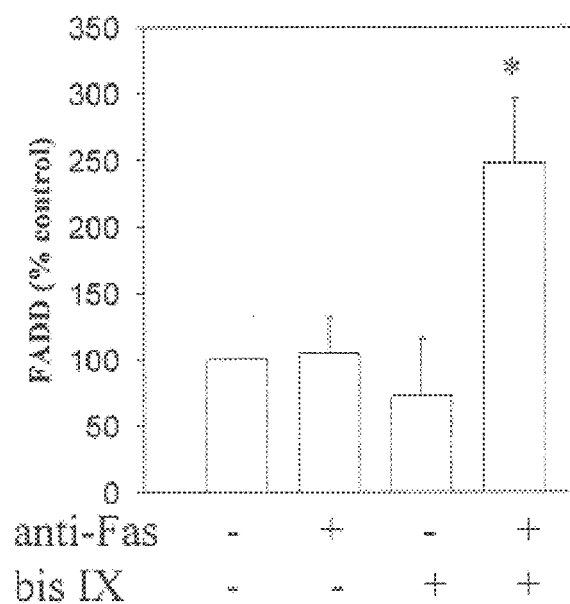
Figure 9

USE OF BISINDOLYLMALEIMIDE COMPOUNDS TO INDUCE FAS-MEDIATED APOPTOSIS

FIELD OF THE INVENTION

The present invention generally relates to a method of inducing apoptosis in cells which may undergo apoptosis. More particularly, the present invention relates to a method of inducing apoptosis in cells by administering to the cells a bisindolylmaleimide compound.

BACKGROUND OF THE INVENTION

Apoptosis, or programmed cell death, is an essential mechanism used throughout life to selectively eliminate cells, and deficient apoptotic cell death is associated with a wide variety of disorders encompassing most cell systems. Jacobson et al., *Cell* 88, 347–354 (1997). Fas (Apo-1/CD95) is a member of the tumor necrosis factor (TNF) receptor family, one of the main signaling systems with the specialized function of inducing apoptosis. Itoh et al., *Cell* 66, 233–243 (1991). Fas is a cell surface receptor that on activation (cross-linkage) by its natural ligand or by an agonistic antibody initiates a signaling cascade that leads to apoptosis. Yonehara et al., *J. Exp. Med.* 169, 1747–1756 (1989); Suda et al., *Cell* 75, 1169–1178 (1993). Impairment of Fas-linked signaling, and thus of apoptosis, appears to contribute to a variety of severe disorders associated, for example, with cell proliferation, inflammation and autoimmunity. Nagata, *Cell* 88, 355–365 (1997). Cancers, such as astrocytomas, which are among the most common lethal brain tumors, can express high levels of Fas and Fas ligand, but although often infiltrated by T cells, such infiltration does not improve patient prognosis, indicating that Fas apoptosis signaling may be dysfunctional. Saas et al., *J. Clin. Invest.* 99, 1173–1178 (1997); Weller et al., *J. Clin. Invest.* 94, 954–964 (1994). Impaired Fas-mediated apoptosis in lpr/lpr mice and gld/gld mice caused by mutations of the Fas or Fas ligand genes, respectively, results in lymphoproliferation and autoimmune disease, indicating that Fas-mediated signaling plays important parts in the induction of lymphocyte apoptosis and in the prevention of autoimmune disease. Watanabe-Fukunaga et al., *Nature* 356, 314–317 (1992); Takahashi et al., *Cell* 76, 969–976 (1994). Activation-induced cell death of T cells mediated by Fas-linked signaling is essential for down-modulating the T-cell response and the elimination of self-reactive T cells. Ju et al., *Nature* 373, 444–448 (1995); Brunner et al., *Nature* 373, 441–444 (1995); Dhein et al., *Nature* 373, 438–441 (1995). Thus, inadequate Fas-mediated apoptosis may contribute to proliferative disorders, and in T cells, could produce loss of T-cell tolerance resulting in the development of autoimmune disease.

The expression of Fas or of Fas ligand can regulate Fas-mediated apoptosis, but it is evident that differences in cell susceptibilities to Fas-mediated apoptosis also can be controlled by the regulation of signaling cascades, because not all Fas-positive cell types undergo apoptosis similarly after stimulation of Fas. Su et al., *Immunity* 2, 353–362 (1995); Miyawaki et al., *J. Immunol.* 149, 3753–3758 (1992). For example, activated T cells are more susceptible to Fas-mediated apoptosis than are naive T cells. Ehl et al., *J. Immunol.* 156, 2357–2360 (1996). Thus, interventions that facilitate Fas-induced apoptosis signaling processes may provide an ideal strategy for enhancing apoptosis for a variety of purposes, such as the elimination of self-reactive T cells in the treatment of autoimmune diseases. One advantage of this approach is that the intervention provides specificity for autoantigen-activated T cells that have failed to undergo activation-induced cell death, whereas the normal immune response to foreign antigens should remain less affected.

Prior art attempts to treat autoimmune diseases have primarily focused on down-regulating deleterious autoimmune reactions without affecting normal immune surveillance. These treatment modalities have focused on either the reestablishment of immune tolerance to autoantigens or to the suppression of T lymphocyte activity using immunosuppressive drugs including cyclosporin A, FK506 or rapamycin. Chatenoud, *Mol. Med. Today* 4, 25–30 (1998). However, these treatment modalities have critical disadvantages including the lack of antigen specificity and the adverse side effects of immunosuppressive therapy including susceptibility to infection and/or disease.

Accordingly, it would be advantageous and desirable to have a method of treatment of autoimmune disorders/diseases which is based on the observation that the total number of autoreactive T lymphocytes depends on a balance between the induction and proliferation of autoimmune T cells and their elimination by activation of an internal suicide program. This suicide program has been termed activation induced cell death (AICD). AICD is initiated in activated lymphocytes following re-stimulation by antigen and involves expression of death inducing ligands and receptors. Accordingly, Applicants have discovered that bisindolylmaleimide compounds can greatly increase the sensitivity of T cells to AICD.

Several bisindolylmaleimide derivatives, which were originally described as inhibitors of protein kinase C (PKC) (Toullec et al., *J. Biol. Chem.*, 266, 1571–1581 (1991); Bit et al., *J. Med. Chem.* 36, 21–29 (1993); Jacobson et al., *J. Pharmacol. Exp. Therap.* 275, 995–1002 (1995); U.S. Pat. No. 5,821,072 to Schwartz et al. (also describes use of bisindolylmaleimides as potentiators of apoptosis in anti-tumor therapy); U.S. Pat. Nos. 5,292,747; 5,481,003; 5,491,242; 5,545,636; 5,552,396; 5,661,173; and 5,672,618), bisindolylmaleimide compounds were found to substantially facilitate Fas-mediated apoptosis in a human astrocytoma cell line and in several human T-cell lines. This facilitation of Fas-mediated apoptosis appears to be independent of PKC inhibition. Facilitation of Fas-mediated apoptosis resulted in increased activation-induced cell death of activated T cells and this effect was specific for Fas- and tumor necrosis factor (TNF)-mediated apoptosis.

The use of some bisindolylmaleimides has been disclosed in the treatment of inflammatory, immunological, bronchopulmonary or cardiovascular disorders (see U.S. Pat. No. 5,057,614 to Davis et al.). In vivo administration of bisindolylmaleimide VIII to rats during autoantigen stimulation was found to almost completely block the development of autoimmune diseases in two models: the Lewis rat model of experimental allergic encephalitis (EAE), and the Lewis adjuvant arthritis model.

SUMMARY OF THE INVENTION

The present invention provides a method of inducing apoptosis in target cells of a subject by administering to the subject a pharmaceutically effective amount of at least one compound of the formula:

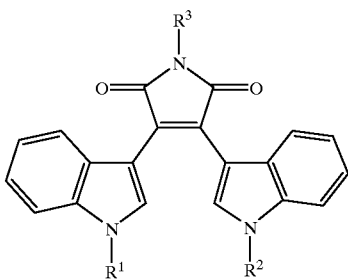

wherein:

R$^1$ is hydrogen, C$_1$–C$_{12}$ alkyl, C$_1$–C$_{12}$ substituted alkyl, C$_3$–C$_7$ heterocycle, or C$_3$–C$_7$ substituted heterocycle, R$^2$ and R$^3$ are independently H or C$_1$–C$_{12}$ alkyl, and the pharmaceutically acceptable salts, esters, amides, and prodrugs thereof, wherein following the administration of the compound(s) of Formula I, the target cell undergoes apoptosis.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

FIGS. 2a–c—Apoptosis analysis of 1321N1 cells. 1321N1 cells were cultured overnight with 100 ng/ml anti-Fas in the absence or presence of 10 μM bisindolylmaleimide VIII (BISVIII). a, 1321N1 cells were stained with annexin V and analyzed by flow cytometry. Open histogram, cells treated with anti-Fas alone; filled histogram, cells treated with anti-Fas and bisindolylmaleimide VIII. Vertical axis, cell number; horizontal axis, fluorescence intensity. b, DNA was extracted from cells treated with anti-Fas (lane 1) or with anti-Fas and bisindolylmaleimide VIII (lane 2) and resolved in 1% agarose gels. DNA laddering was evident after treatment with anti-Fas and bisindolylmaleimide VIII (lane 2) but not after treatment with only anti-Fas (lane 1). c, TUNEL staining of cytospin preparations, showing that treatment with anti-Fas plus bisindolylmaleimide VIII (right panel), but not with anti-Fas alone (left and center panels) resulted in positive staining in most cells.

FIGS. 5a–c—Potentiation of Fas-mediated apoptosis by bisindolylmaleimide VIII in human T-cell lines. Human CEM-6 (a), Jurkat (b) and Molt-4 (c) T cells were cultured (1×10$^6$ cells/ml) in the presence of 10 μM bisindolylmaleimide VIII and/or 100 ng/ml anti-Fas antibody for the indicated times (horizontal axes). Apoptosis was determined by flow cytometry analysis using Hoechst 33342. ○, anti-Fas; □, bisindolylmaleimide VIII; ●, both reagents. Values shown are mean±s.e.m. of three independent experiments.

FIG. 9—Recruitment of FADD in 1321N1 cells treated with anti-Fas and bisindolylmaleimide IX. (A) Representative immunoblot of membrane-associated FADD in cells treated with bisindolylmaleimide IX, anti-Fas, or both agents. (B) Representative immunoblot and quantitation of FADD detected in immunoprecipitates of Fas. Cells were treated with bisindolylmaleimide IX, anti-Fas, or both agents, Fas was immunoprecipitated, and immunoblots of FADD were prepared. Treatment with both anti-Fas and bisindolylmaleimide IX increased the coprecipitation of FADD with Fas, whereas each agent alone was ineffective.

DETAILED DESCRIPTION OF THE INVENTION

Figure 1:
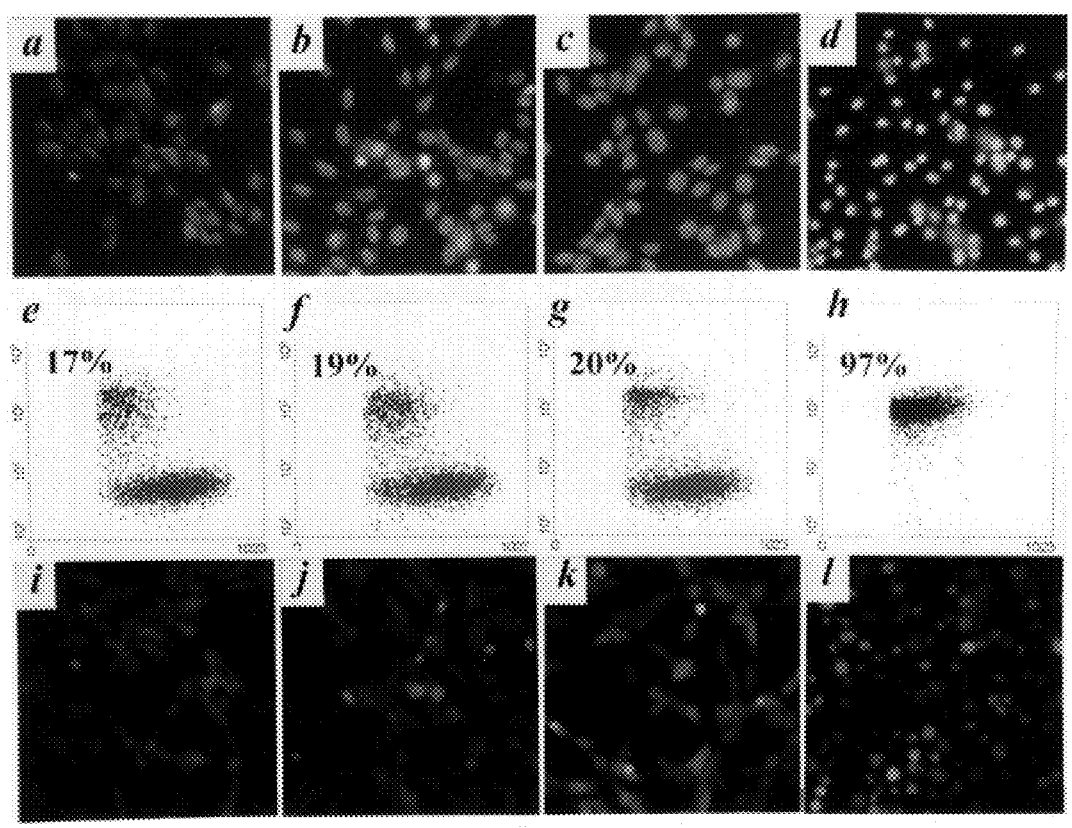
FIGS. 1a–l—Bisindolylmaleimide VIII enhances apoptosis induced by anti-Fas antibody in 1321N1 cells. 1321N1 cells were cultured overnight with control medium (a, e and i), 100 ng/ml anti-Fas antibody (b, f and j), 10 μM bisindolylmaleimide VIII (c, g and k) or both anti-Fas antibody and bisindolylmaleimide VIII (d, h and l). a–d, Cells were stained with Hoechst 33342 and examined under ultraviolet fluorescence; a–c show staining of healthy cells, and d shows the staining of condensed nuclei indicative of cell death. Original magnification, ×400. e–h, For each treatment group 10,000 cells were analyzed by FACSvantage. Green dots indicate apoptotic cells; red dots indicate healthy cells. Percentages indicate the proportion of cell populations that were apoptotic. i–l, Cells were stained with a live/dead cell staining kit and examined by fluorescence microscopy. Healthy cells are stained green; dead or dying cells are stained red. Original magnification, ×400.

The present invention provides methods of using at least one compound having the Formula I:

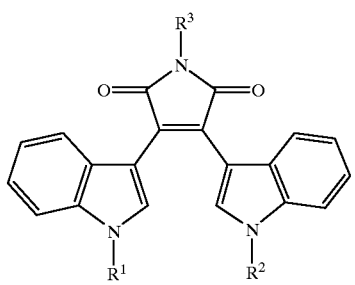

I wherein:
R$^1$ is hydrogen, C$_1$–C$_{12}$ alkyl, C$_1$–C$_{12}$ substituted alkyl, C$_3$–C$_7$ heterocycle, or C$_3$–C$_7$ substituted heterocycle;

R$^2$ and R$^3$ are independently H or C$_1$–C$_{12}$ alkyl; and the pharmaceutically acceptable salts, esters, amides, and prodrugs thereof, to facilitate and/or induce apoptosis including Fas-mediated apoptosis and/or to inhibit T cell-mediated autoimmune diseases or disorders.

The present invention also provides a method of treating a subject having a T cell mediated autoimmune disorder by administering to a subject having a T cell mediated autoimmune disorder characterized by defective or insufficient activation-induced cell death of activated autoreactive T cells, a pharmaceutically effective amount of at least one compound of the Formula I:

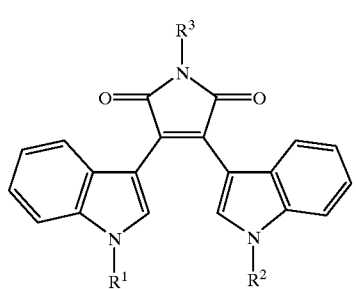

I wherein:
R$^1$ is hydrogen, C$_1$–C$_{12}$ alkyl, C$_1$–C$_{12}$ substituted alkyl, C$_3$–C$_7$ heterocycle, or —C$_3$–C$_7$ substituted heterocycle;

R$^2$ and R$^3$ are independently H or C$_1$–C$_{12}$ alkyl; and the pharmaceutically acceptable salts, esters, amides, and prodrugs thereof, wherein administration of the at least one compound of formula I causes activation-induced cell death of the activated autoreactive T cells.

The present invention further provides a method of preventing T cell tolerance in a subject by eliminating activated T cells having impaired Fas-mediated apoptosis by administering a pharmaceutically effective amount of at least one compound of the Formula I:

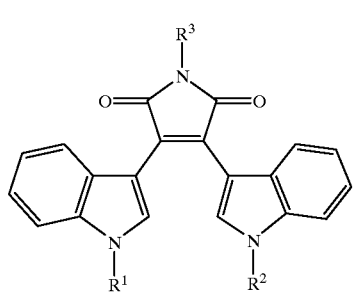

I wherein:
R$^1$ is hydrogen, C$_1$–C$_{12}$ alkyl, C$_1$–C$_{12}$ substituted alkyl, C$_3$–C$_7$ heterocycle, or C$_3$–C$_7$ substituted heterocycle;

R$^2$ and R$^3$ are independently H or C$_1$–C$_{12}$ alkyl; and the pharmaceutically acceptable salts, esters, amides, and prodrugs thereof, wherein following the administering step, the activated T cells having impaired Fas-mediated apoptosis are caused to undergo apoptosis.

The present invention further provides a method of facilitating Fas-mediated intracellular signaling in a cell by administering to the cell a pharmaceutically effective amount of at least one compound of a Formula I:

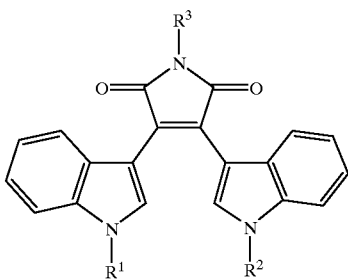

I wherein:
R$^1$ is hydrogen, C$_1$–C$_{12}$ alkyl, C$_1$–C$_{12}$ substituted alkyl, C$_3$–C$_7$ heterocycle, or —C$_3$–C$_7$ substituted heterocycle;
R$^2$ and R$^3$ are independently H or C$_1$–C$_{12}$ alkyl; and the pharmaceutically acceptable salts, esters, amides, and prodrugs thereof.

The preferred compounds for use in the methods of the present invention are generically referred to as bisindolylmaleimides and have the general structure as shown in Formula I. Preferred bisindolylmaleimides according to the present invention include, but are not limited to, bisindolylmaleimide I, 2-[1-(3-Dimethylaminopropyl)-indol-3-yl]-3-(1H-indol-3-yl)maleimide; bisindolylmaleimide II, 2-[1-[2-(1-Methylpyrrolidinyl)ethyl]indol-3-yl]-3-(1H-indol-3-yl)maleimide; bisindolylmaleimide III, 2-[1-(3-Aminopropyl)-indol-3-yl]-3-(indol-3-yl)maleimide; bisindolylmaleimide IV, 2,3-bis(1H-indol-3-yl)maleimide; bisindolylmaleimide V, 2,3-bis(1H-indol-3-yl)-N-methylmaleimide; bisindolylmaleimide VI, 2-[1-(2-Piperidin-2-yl)ethyl]-1H-indol-3-yl]-3-(1H-indol-3-yl)maleimide; bisindolylmaleimide VII, 2-[1-(3-Piperazinopropyl)-1H-indol-3-yl]-3-(1H-indol-3-yl)maleimide; bisindolylmaleimide VIII, 2-[1-(3-Aminopropyl)indol-3-yl]-3-(1-methylindol-3-yl)maleimide; bisindolylmaleimide IX, 2-[1-[3-(Amidinothio)propyl]-1H-indol-3-yl]-3-(1-methylindol-3-yl)maleimide; bisindolylmaleimide X, 2-(8-Aminomethyl)-6,7,8,9-tetrahydropyrido[1,2-a]indol-3-yl]-3-(1-methylindol-3-yl)maleimide; and bisindolylmaleimide XI, 2-(8-Dimethylamino)methyl)-6,7,8,9-tetrahydropyrido[1,2-a]indol-3-yl)-3-(1-methylindol-3-yl)maleimide and combinations thereof The most preferred of these compounds for use in the methods of the present invention are bisindolylmaleimides VIII and IX. Other preferred bisindolylmaleimides include bisindolylmaleimide III, X and XI. Other bisindolylmaleimide compounds or derivatives can include those compounds disclosed in U.S. Pat. No. 5,380,756 to Barth et al.

Conditions or diseases that could be treated using the present invention include autoimmune diseases, cancer or any other hyperproliferative diseases, conditions associated with inflammation or cell activation, including inflammation or cell proliferation in the brain and including conditions with activated astrocytes and/or microglia.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The symbol "–" means a bond.

The term "patient" or "subject" means all animals including humans. Examples of patients include humans, cows, dogs, cats, goats, sheep, and pigs.

The term "substituted" means that the base organic radical has one or more substituents. For example, substituted cyclohexyl means a cyclohexyl radical that has one or more substituents. Substituents include, but are not limited to, halogen, C$_1$–C$_6$ alkyl, —CN, CF$_3$, —NO$_2$, —NH$_2$, —NHC$_1$–C$_8$ alkyl, —N(C$_1$–C$_8$ alkyl)$_2$, —OC$_1$–C$_8$alky, and —OH.

The term "heterocycle" means a cycloalkyl group wherein one or more carbon atom is replaced with a heteroatom. Examples of heterocycles include, but are not limited to, pyrrolidinyl, piperidinyl, and piperazinyl.

Those skilled in the art are easily able to identify patients having a condition associated with impaired Fas-mediated apoptosis such as a cancer or an autoimmune disorder/disease wherein activated T cells fail to undergo activation induced cell death or apoptosis. For example, patients who have a cancer such as astrocytoma or glioma.

The term "impaired" means that a patient's or subject's normal cellular mechanism for apoptosis or programmed cell death is not functioning properly resulting in a disease or an abnormal condition such as a cancer, immunologic or autoimmune disorder/disease, or inflammation.

A therapeutically effective amount is an amount of a compound of Formula I, that when administered to a patient or subject, ameliorates a symptom of the disease, disorder, or condition.

The term "apoptosis" means programmed cell death and includes the term "activation induced cell death" to describe the process by which activated lymphocytes (e.g. T cells), following re-stimulation by an antigen, express cell death inducing ligands and receptors.

The compounds of the present invention can be administered to a patient or subject either alone or as part of a pharmaceutical composition. The compositions can be administered to patients either orally, rectally, parenterally (intravenously, intramuscularly, or subcutaneously), intracisternally, intravaginally, intraperitonally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the compositions can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobroride, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate and laurylsulphonate salts, and the like. These may include cations based on the alkalai and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci.,* 1977; 66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Prodrugs as Novel Delivery Systems," Vol. 14 of the A.C.S. Symposium Series, and in *Bioreversible Carriers in Drug Design,* ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels, for example, for a normal human adult having a body weight of about 70 kilograms, a dosage in the range of about 100 μg to about 500 μg per dose is preferable and can be given every other day. For example, the dosage can depend on a number of factors including the requirements of the patient, the severity of the condition being treated, and the pharmacological activity of the compound being used. The determination of optimum dosages for a particular patient is well known to those skilled in the art.

In addition, it is intended that the present invention cover compounds made either using standard organic synthetic techniques, including combinatorial chemistry or by biological methods, such as through metabolism.

The present invention also includes a kit containing the bisindolylmaleimide compounds of Formula I and can also include any reagents or components necessary for the administration of the compounds.

The experimental data presented below are intended to illustrate particular embodiments of the invention and are not intended to limit the scope of the specification, including the claims, in any way.

EXPERIMENTAL

Materials and Methods

Cell lines and reagents: Human 1321N1 astrocytoma cells were a gift from J. H. Brown (University of California at San Diego), and the human T-cell leukemia cell lines, Jurkat, CEM-6 and Molt-4, were purchased from American Type Culture Collection (Rockville, Md.). Bisindolylmaleimides I, II, III, IV, V, VIII, IX, X AND XI, H7, calphostin C, and chelerythrine chloride were purchased from Alexis Biochemicals (San Diego, Calif.). Anti-human Fas antibody (clone: CH11) was purchased from Upstate Biotechnology (Lake Placid, N.Y.).

Induction of apoptosis: 1321N1 cells were grown in 48-well tissue culture plates in 5% FCS-DMEM to 70% confluence. The human T-cell lines ($1 \times 10^6$ of log phase cells) were plated in 24-well plates in 1 ml of 12% FCS, RPMI-1640. Cells were incubated overnight, or for various times, with medium, anti-Fas antibody alone, bisindolylmaleimides or other test agents alone, or anti-Fas and bisindolylmaleimide or other agents together at various concentrations.

Detection of apoptosis: Cell death or apoptosis was determined by several methods. For cells in culture, the Live/Dead cell staining kit (Molecular Probes, Eugene, Oreg.) was used according to the manufacturer's instructions. Stained cells were examined using an inverted fluorescence microscope. For Hoechst apoptosis staining and flow cytometric analysis, $5 \times 10^5 - 10 \times 10^5$ cells were stained with 20μ of 100 ng/ml Hoechst 33342 dye (Sigma) at room temperature for twenty minutes. After washing, the cells were fixed in 1% paraformaldehyde solution, and 10,000 ungated cells were analyzed by FACSvantage with a UV filter. For annexin V staining of apoptotic cells and flow cytometric analysis, FITC-conjugated annexin V (PharMingen, San Diego, Calif.) was used according to the manufacturer's instructions, and 10,000 cells were analyzed by FACSvantage. For DNA laddering, high molecular weight DNA was extracted from cells using phenol-chloroform and was then resolved in 1% agarose gels and stained with ethidium bromide. Finally, TdT-mediated dUTP nick-end labeling (TUNEL) was done according to the manufacturer's instructions (Amersham).

T-cell activation and induction of apoptosis: Splenic T cells were isolated from C57BL/6(B6)+/+ and lpr/lpr mice four to six weeks old using T-cell enrichment columns (R&D System, Minneapolis, Minn.). Purified T cells ($5 \times 10^6$ cells/ml) were cultured in plates precoated with 5 μg/ml anti-CD3 antibody (clone: F500; PharMingen, San Diego, Calif.) for forty-eight hours. The proliferative T cells were collected on Ficoll-Hypaque (d=1.077) and cultured in 100 u/ml of interleukin-2 for three days. The T cells were then re-stimulated overnight with anti-CD3 in the presence or absence of bisindolylmaleimide VIII. Apoptosis was determined by Hoechst 33342 staining and flow cytometric analysis. Freshly isolated T cells that were not stimulated with anti-CD3 were used as non-activated controls.

$^{51}$CR release assay for Fas ligand activity: Activated T cells from wild-type and lpr/lpr mice were re-stimulated with anti-CD3 antibody overnight in the presence or absence of bisindolylmaleimide VIII (as described above). Viable T cells were collected on Ficoll and used as effector cells for measuring Fas ligand activity. Fas ligand-sensitive A20 cells were used as the target cells and were labeled with $^{51}$Cr. T cells ($5 \times 10^5$) were co-cultured with A20 cells ($5 \times 10^4$) in 96-well round-bottom plates for eight hours. A20 cells were cultured in medium to measure spontaneous release, or in medium containing 0.1% SDS to measure maximum release. The supernatants were collected and radioactivity was assessed using a γ-counter. Fas ligand activity was calculated as the specific release of $^{51}$CR from A20 cells using the following equation: specific release (%)=(cpm of sample-cpm of spontaneous release)/(cpm of maximum release-cpm of spontaneous release).

Induction of autoimmune disease and treatment with bisindolylmaleimide VIII: For induction of EAE, female Lewis rats six weeks old (Jackson Laboratory, Bar Harbor, Me.) were immunized with 50 μg MBP (Sigma) in Freund's complete adjuvant (Difco, Detroit, Mich.) on day 0. Rats were injected intramuscularly with 250 μg bisindolylmaleimide VIII (dissolved in 10% DMSO-PBS) or vehicle. The treatment was started on day 1 and was repeated every other day for five doses. The development of EAE was evaluated every day for ten days after onset; a clinical score was assigned to each individual rat as described: 0, no disease; 1, loss of tail tone; 2, complete loss of tail tone; 3, lower leg paralysis; 4, paralysis. Sun et al., *Nature* 332, 843–845 (1988). Onset was determined as the day each rat achieved a clinical score of 1 or more, and the clinical score was reported as the average maximum achieved by each rat that attained a score of 1 or more.

For induction of adjuvant arthritis, male Lewis rats eight weeks old were immunized with 0.2 ml complete Freund's adjuvant at the base of the tail. The treatments with bisindolylmaleimide and control vehicle were exactly as used in the EAE model. Rats were killed thirty days after immunization and all joints were fixed in formalin and processed for histological evaluation to assess severity of arthritis. Histological lesions were evaluated for synovial proliferation, mononuclear cell infiltration, cartilage erosion and bone destruction as follows: 1, minor synovial proliferation; 2, severe synovial proliferation and inflammatory cell infiltration; 3, cartilage erosion; 4, bone destruction. Any joint showing any lesion was counted as positive; the severity score was reported as the average maximum achieved by each rat that attained a score of 1 or more.

The MOG peptide immunization and T-cell proliferative response: Female C57BL/6−+/+ and lpr/lpr mice six weeks old were immunized with 75 μg MOG peptide 25–35 in Freud's complete adjuvant (Sun et al., Nature 332, 843–845 (1988)), and were given 250 μg bisindolylmaleimide VIII (intraperitoneally) on day 3 after immunization and every other day for a total of three treatments. Ten days after immunization, splenic T cells were isolated and stimulated with 10 μg/ml MOG peptide or 1 μg/ml anti-CD3 antibody in 96-well round-bottomed plates. The T-cell proliferative response was determined by measuring $^3$H-thymidine incorporation at seventy-two hours after stimulation.

Results

Bisindolylmaleimide potentiates Fas-mediated apoptosis. Examination of cells that were stimulated with anti-Fas antibody alone or with bisindolylmaleimide VIII showed that bisindolylmaleimide VIII converted human astrocytoma 1321N1 cells from being essentially entirely resistant to apoptosis mediated by Fas to being highly sensitive to it. Although 1321N1 cells express functional Fas receptors on the cell surface (data not shown), they are relatively resistant to apoptosis induced by anti-Fas antibody. Thus, an overnight incubation of 1321N1 cells with a low concentration of agonistic anti-Fas antibody (100 ng/ml) had no detectable effect on cell morphology or survival compared with that of cells maintained in growth medium (see FIGS. 1a and b). Incubation with 10 μM bisindolylmaleimide VIII alone also had no detectable effect (see FIG. 1c). In contrast, after incubation with both anti-Fas antibody and bisindolylmaleimide VIII essentially all cells were round, membrane blebbing was apparent, and the cells had condensed nuclei, all changes that are typical of apoptosis (see FIG. 1d). The condensed apoptotic nuclei were quantitatively analyzed by ultraviolet flow cytometry. This analysis confirmed that compared with control cells (see FIG. 1e) neither anti-Fas antibody (see FIG. 1f) nor bisindolylmaleimide VIII (see FIG. 1g) alone affected the cells. However, incubation of 1321N1 cells with 100 ng/ml of anti-Fas antibody in the presence of 10 μM bisindolylmaleimide VIII resulted in the induction of apoptosis in nearly 100% of the cells (see FIG. 1h). The use of Calcein AM and ethidium homodimer-1 to distinguish live cells from dead cells in culture also confirmed that the proportion of healthy cells detected in control medium (see FIG. 1i) was unaffected by anti-Fas antibody (see FIG. 1j) or bisindolylmaleimide VIII (see FIG. 1k), but that combined treatment with anti-Fas antibody and bisindolylmaleimide VIII resulted in the death of most cells (see FIG. 1l).

Apoptotic cell death of 1321N1 cells treated with both anti-Fas antibody and bisindolylmaleimide VIII was further verified by Annexin V staining, DNA laddering and TUNEL staining (see FIG. 2). These results demonstrate that although bisindolylmaleimide VIII alone was not cytotoxic, it greatly potentiated Fas-mediated apoptosis, converting the Fas apoptosis resistant state of 1321N1 cells to a very sensitive state, indicating that bisindolylmaleimide VIII enhances the apoptosis signal generated by stimulation of Fas.

Figure 3:
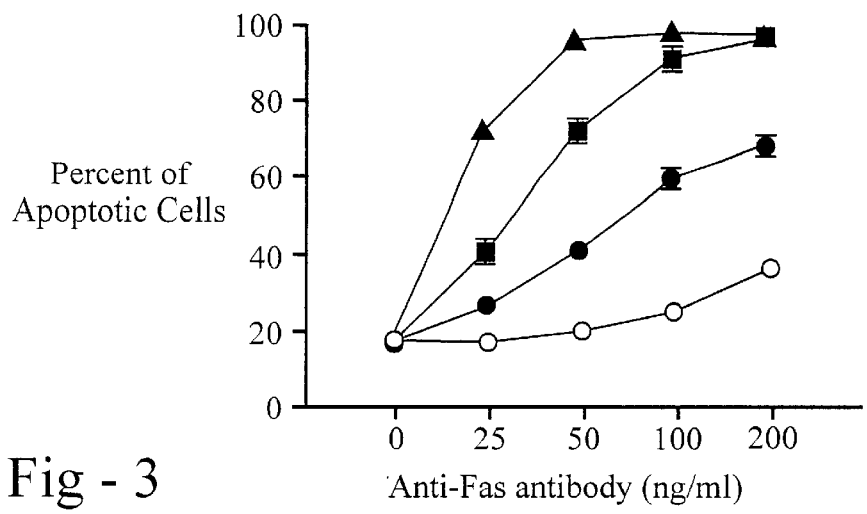
FIG. 3—Dose dependencies of bisindolylmaleimide VIII and anti-Fas antibody on potentiation of apoptosis. 1321N1 cells were incubated overnight with the indicated concentrations of anti-Fas antibody (horizontal axis) and 0 μM (○), 1 μM (●), 3 μM (■), or 10 μM (▲) bisindolylmaleimide VIII. Apoptosis was determined by flow cytometry analysis using Hoechst 33342. Values shown are mean±s.e.m. of three independent experiments.

Concentration dependence of Fas-mediated apoptosis. The dose dependencies of anti-Fas antibody and bisindolylmaleimide VIII on apoptosis of 1321N1 cells were determined by measuring apoptosis in cells exposed to varying concentrations of each agent using Hoechst 33342 staining to quantify apoptotic cells. In the absence of anti-Fas antibody, 1, 3 or 10 μM bisindolylmaleimide VIII did not have a substantial effect on apoptosis (see FIG. 3). Similarly, in the absence of bisindolylmaleimide VIII, anti-Fas antibody at concentrations less than 100 ng/ml had little effect on apoptosis of 1321N1 cells (see FIG. 3). However, in the presence of bisindolylmaleimide VIII, there was a large increase in apoptosis induced by anti-Fas antibody. This effect of bisindolylmaleimide VIII on apoptosis induced by anti-Fas antibody was dose-dependent, with higher concentrations of bisindolylmaleimide VIII resulting in greater apoptosis induced by anti-Fas antibody. Thus, with 100 ng/ml anti-Fas antibody, the potentiating effect was clearly evident with a concentration of bisindolylmaleimide VIII as low as 1 μM, and nearly complete apoptosis was obtained with 3 μM bisindolylmaleimide VIII. The potentiation by bisindolylmaleimide VIII also was dependent on the dose of anti-Fas antibody. For example, with 3 μM bisindolylmaleimide VIII, apoptosis was induced in more than 70% of 1321N1 cells by 50 ng/ml anti-Fas antibody. Thus, bisindolylmaleimide VIII decreased the threshold for apoptosis triggered by anti-Fas antibody in a concentration-dependent manner.

Figure 4C:
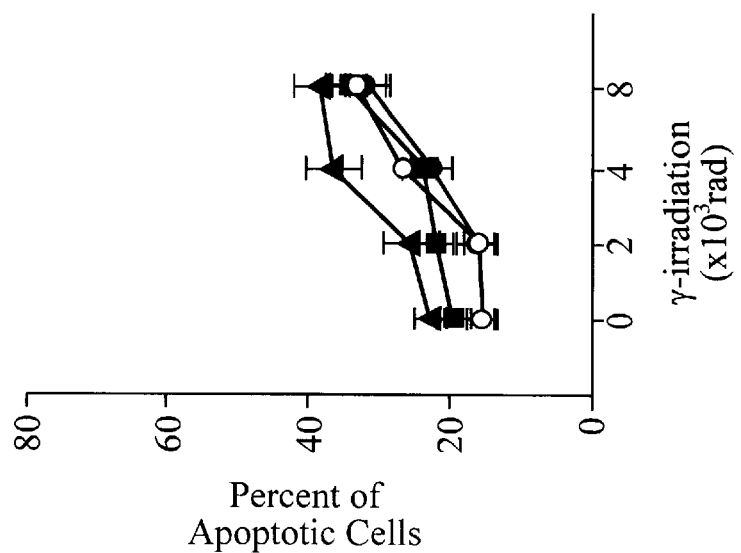
FIGS. 4a–c—Effect of bisindolylmaleimide VIII on apoptosis of 1321N1 cells induced by TNF-α, dexamathsone or gamma-irradiation. 1321N1 cells were incubated overnight with the indicated concentrations (horizontal axes) of TNF-α (a) or dexamathsone (b) in the presence of bisindolylmaleimide VIII; for gamma-irradiation (c), cells were irradiated at the indicated dose and incubated overnight with bisindolylmaleimide VIII. Apoptosis was determined by flow cytometry analysis using Hoechst 33342. ○, 0 μM bisindolylmaleimide VIII; ●, 1 μM; ■, 3 μM; ▲, 10 μM. Values shown are mean±s.e.m. of three independent experiments.
Figure 4B:
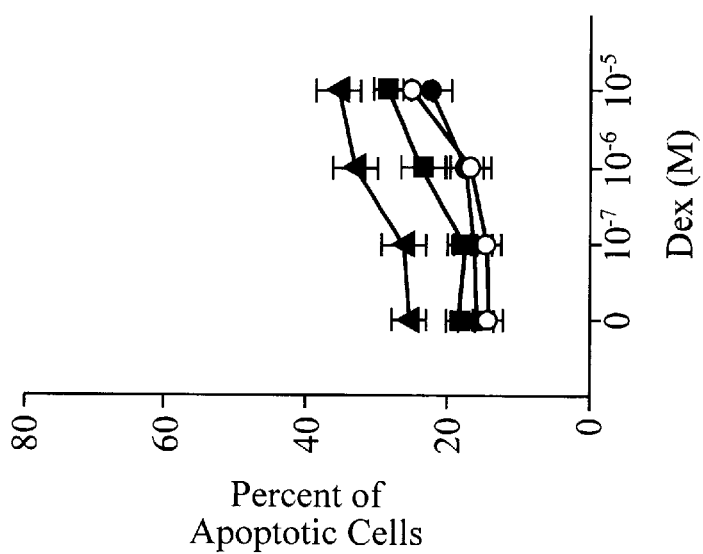
Figure 4A:
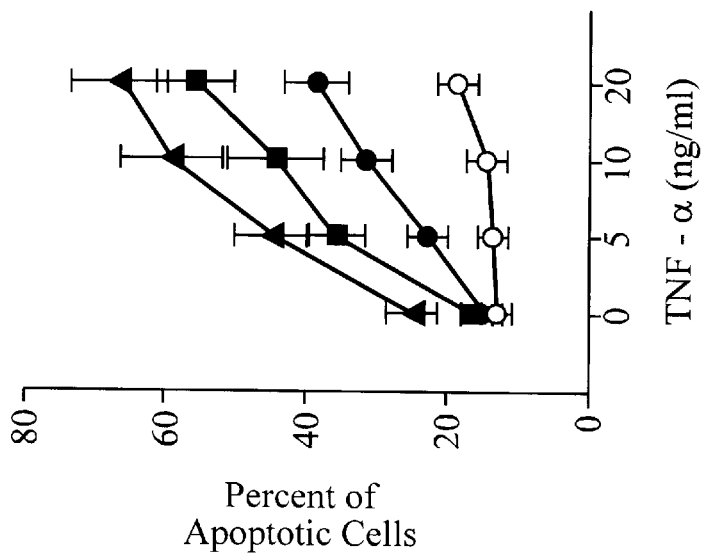

Bisindolylmaleimide potentiates TNF-mediated apoptosis. To determine if the potentiation of apoptosis induced by bisindolylmaleimide VIII is specific for Fas, the effects of bisindolylmaleimide VIII on apoptosis of 1321N1 cells triggered by other apoptosis inducers were examined, including TNF-α (to activate the TNF receptor, which belongs to the same receptor family as Fas), dexamethasone and irradiation. Bisindolylmaleimide VIII also enhanced apoptosis induced by TNF-α (see FIG. 4). In the absence of bisindolylmaleimide VIII, 1321N1 cells were resistant to apoptosis mediated by TNF-α, as treatment with 5–20 ng/ml TNF-α caused no substantial increase in apoptosis (less than a 10% increase in apoptotic cells). Incubation with bisindolylmaleimide VIII facilitated apoptosis induced by TNF-α in a concentration-dependent manner, with 20 ng/ml TNF-α inducing apoptosis in over 60% of the cells in the presence of 10 μM bisindolylmaleimide VIII (see FIG. 4a). In contrast, bisindolylmaleimide VIII had little effect on apoptosis of 1321N1 cells treated with dexamethasone (see FIG. 4b) or irradiation (see FIG. 4c). These results indicate that bisindolylmaleimide VIII selectively facilitates apoptosis signal transduction mechanisms induced by activation of the TNF receptor family.

Apoptosis with bisindolylmaleimides is PKC independent. Given the large potentiation of Fas-induced apoptosis by bisindolylmaleimide VIII, it was next determined whether other bisindolylmaleimide derivatives had a similar effect, and if this interaction was related to inhibition of PKC. The effects of several bisindolylmaleimide derivatives and of other PKC inhibitors on Fas-mediated apoptosis in 1321N1 cells were assessed. Nine bisindolylmaleimide derivatives were tested, all of which (except for bisindolylmaleimide V) are relatively equally potent inhibitors of PKC, at a concentration of 10 μM as shown in Table 1. Bisindolylmaleimides VIII and IX produced the greatest potentiation, increasing apoptosis induced by 100 ng/ml anti-Fas antibody from the basal level of near 19% to almost complete apoptosis (94%), an approximately five-fold increase. Bisindolylmaleimides III, X and XI produced intermediate potentiation, as demonstrated by the 2.2- to 3.6-fold increases in Fas-mediated apoptosis (from basal levels of 18–21% to treated levels of 45–66% apoptotic cells). Bisindolylmaleimides I, II and IV did not potentiate Fas-mediated apoptosis, although they are also potent inhibitors of PKC. Three other PKC inhibitors structurally unrelated to the bisindolylmaleimides (H7, calphostin C, and chelerythrine chloride) failed to potentiate Fas-mediated apoptosis. These results indicate that inhibition of PKC cannot account for the potentiation by bisindolylmaleimide VIII and IX of Fas-mediated apoptosis.

Potentiation of Fas-mediated apoptosis in T cells. The investigation of the effects of bisindolylmaleimide VIII was extended to T cells, because Fas-mediated apoptosis is well recognized as being essential for the maintenance of T-cell tolerance and in preventing the development of autoimmune diseases. Watanabe-Fukunaga et al., Nature 356, 314–317 (1992); Takahashi et al., Cell 76, 969–976 (1994). Therefore, it was determined if bisindolylmaleimide VIII also facilitates Fas-mediated apoptosis in T cells using three human T-cell lines known to have different sensitivities to apoptosis induced by anti-Fas antibody. CEM-6 cells showed a moderate apoptotic response to anti-Fas antibody (100 ng/ml); bisindolylmaleimide VIII (10 μM) alone had no effect at two and four hours, but apoptosis was slightly increased after eight hours (see FIG. 5a). Exposure to both agents together more than doubled Fas-mediated apoptosis at two, four and eight hours. Jurkat cells showed a slight apoptotic response to anti-Fas antibody (100 ng/ml); bisindolylmaleimide VIII (which had no effect alone) greatly increased apoptosis induced by anti-Fas antibody, which reached 78% by eight hours, compared with only 24% in the absence of bisindolylmaleimide VIII (see FIG. 5b). Molt-4 cells were resistant to anti-Fas antibody in the absence of bisindolylmaleimide VIII, but incubation with both agents increased apoptotic cells to 54% at eight hours, compared with 10% after exposure to either anti-Fas antibody or bisindolylmaleimide VIII alone (see FIG. 5c). These results demonstrate that bisindolylmaleimide VIII greatly facilitates Fas-mediated apoptosis in human T cells, and that this effect occurs irrespective of the cell's basal sensitivity to apoptosis induced by anti-Fas antibody.

TABLE 1

Effect of bisindolylmaleimide derivatives and other PKC inhibitors on anti-Fas antibody induced apoptosis

| Agents | Dose (μM) | Apoptosis (%) Without anti-Fas | With anti-Fas | Potentiation Index |
|---|---|---|---|---|
| Medium | — | 18.5 ± 3.5 | 22.1 ± 2.9 | 1.19 |
| Bisindolylmaleimide I | 10 | 25.2 ± 4.2 | 27.8 ± 3.1 | 1.10 |
| Bisindolylmaleimide II | 10 | 19.2 ± 3.6 | 24.2 ± 3.2 | 1.26 |
| Bisindolylmaleimide III | 10 | 20.5 ± 2.6 | 44.5 ± 4.1 | 2.17 |
| Bisindolylmaleimide IV | 10 | 21.5 ± 2.8 | 24.5 ± 3.8 | 1.14 |
| Bisindolylmaleimide V | 10 | 18.9 ± 3.1 | 26.5 ± 3.2 | 1.40 |
| Bisindolylmaleimide VIII | 10 | 19.8 ± 2.4 | 92.5 ± 12.1 | 4.7 |
| Bisindolylmaleimide IX | 10 | 18.2 ± 2.3 | 95.2 ± 14.6 | 5.2 |
| Bisindolylmaleimide X | 10 | 18.2 ± 2.6 | 65.9 ± 8.9 | 3.6 |
| Bisindolylmaleimide XI | 10 | 21.3 ± 2.5 | 59.5 ± 11.2 | 2.8 |
| H7 | 10 | 28.6 ± 3.4 | 32.1 ± 4.7 | 1.12 |
| calphostin C | 10 | 22.5 ± 3.2 | 25.6 ± 3.6 | 1.14 |
| Chelerythrine chloride | 10 | 72.5 ± 15.6 | 73.5 ± 16.3 | 1.01 |

1321 N1 cells were cultured overnight with each agent at the indicated concentration in the absence or presence of anti-Fas antibody. Apoptosis was determined by flow cytometry using Hoechst 33342 staining. The potentiation index was calculated as the following ratio of apoptotic cells: (test agent with anti-Fas)/(test agent without anti-Fas). Each value is the mean ±s.e.m. of three independent experiments.

Figure 6C:
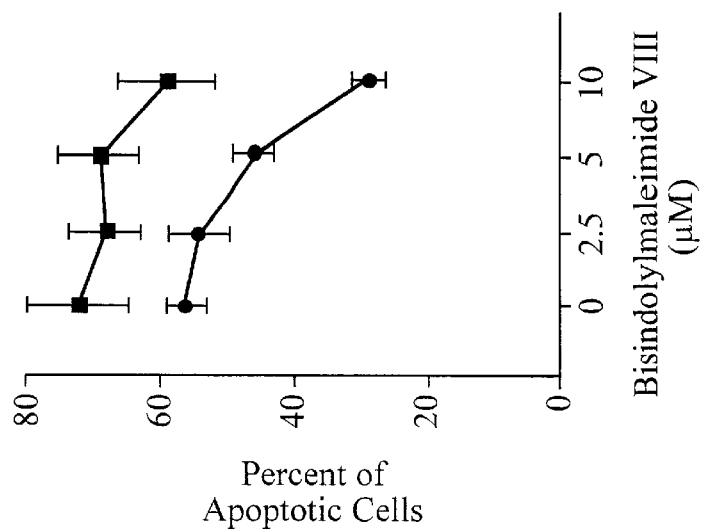
FIGS. 6a–c—Bisindolylmaleimide VIII enhances activation-induced cell death in T cells in a Fas-dependent fashion. T cells were isolated from spleens of C57BL/6 (B6)+/+ (a) and lpr/lpr (b) mice. The T cells were stimulated with plate-bound anti-CD3 antibody for forty-eight hours. Activated T cells were collected and maintained in the presence of interleukin-2 for three days, then re-stimulated overnight with anti-CD3 antibody in the presence of the indicated concentrations (horizontal axes) of bisindolylmaleimide VIII. To determine if the enhanced apoptosis is specifically mediated by Fas, 100 μg/ml soluble Fas-Lg fusion protein was added to the cultures of T cells from B6–+/+ mice. Freshly isolated spleen T cells without previous anti-CD3 stimulation were used as non-activated T cells. Apoptosis was determined by flow cytometry using Hoechst 33342 staining. ●, activated; ■, activated+Fas-Lg; ○, non-activated. Values shown are mean±s.e.m. of T cells from three to five mice. c, Effect of bisindolylmaleimide VIII on Fas ligand expression. T cells re-stimulated by anti-CD3 antibody (as described above), from B6–+/+ and –lpr/lpr mice, were analyzed for Fas ligand expression using the $^{51}$Cr-release assay. Viable T cells were incubated with $^{51}$Cr-labeled A20 cells (at a ratio of 1:10) for eight hours and Fas ligand activity was determined as the specific release of $^{51}$Cr from A20 cells. Filled circles, B6–+/+; filled squares, B6–lpr/lpr. Values shown are means of triplicate cultures.
Figure 6B:
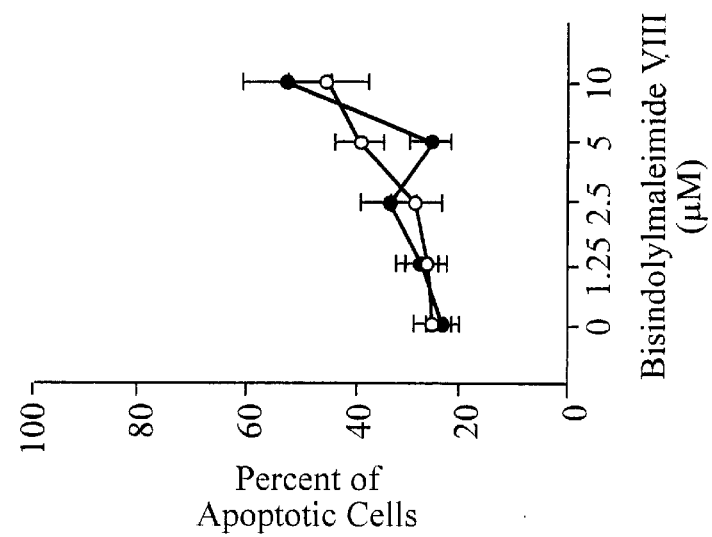
Figure 6A:
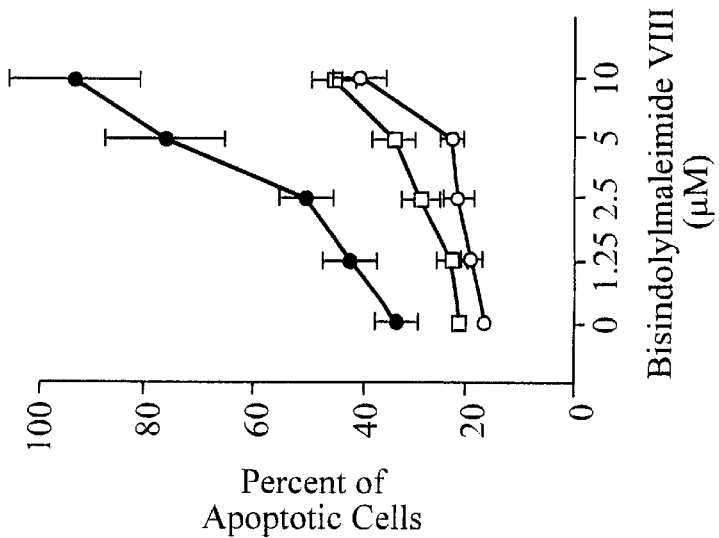

Facilitation of activation-induced cell death of T cells. After activation, T cells express increased levels of both Fas and Fas ligand, and apoptosis mediated by Fas and Fas ligand is the main mechanism underlying activation-induced cell death of T cells. Ju et al., Nature 373, 444–448 (1995); Brunner et al., Nature 373, 441–444 (1995); Dhein et al., Nature 373, 438–441 (1995). Thus, if bisindolylmaleimide VIII facilitates signaling linked with Fas-induced apoptosis, bisindolylmaleimide VIII should promote activation-induced cell death of activated T cells. To test this, splenic T cells were isolated from wild-type mice and activated them using anti-CD3 antibody. Bisindolylmaleimide VIII greatly increased apoptosis of the activated T cells from wild-type mice in a dose-dependent manner, with almost 100% of the T cells stimulated by anti-CD3 antibody undergoing apoptosis in the presence of 10 μM bisindolylmaleimide VIII, compared with only 34% in the absence of bisindolylmaleimide VIII (see FIG. 6a). Increased apoptosis of activated T cells in the presence of bisindolylmaleimide VIII was mediated mainly by Fas; soluble Fas-Ig fusion protein essentially completely blocked the increased apoptosis (see FIG. 6a). Moreover, apoptosis of non-activated T cells was only slightly affected (see FIG. 6a), indicating that enhanced apoptosis in activated T cells by bisindolylmaleimide VIII is Fas-dependent. Bisindolylmaleimide VIII only slightly increased apoptosis in either activated or non-activated T cells from lpr/lpr mice (see FIG. 6b). This result also supports the conclusion that the increase in activation-induced cell death of T cells elicited by bisindolylmaleimide VIII is dependent on Fas-mediated apoptosis. To determine if the potentiation by bisindolylmaleimide VIII of Fas-mediated apoptosis in activated T cells could result from increased production of Fas ligand, a $^{51}$Cr release assay was used to measure Fas ligand activity of the T cells after anti-CD3 re-stimulation. In the presence of bisindolylmaleimide VIII, Fas ligand activity was decreased in activated T cells from wild-type mice, which correlated with the increased cell death caused by bisindolylmaleimide VIII. In contrast, there was little effect of bisindolylmaleimide VIII on Fas ligand activity in activated T cells from lpr/lpr mice (see FIG. 6c). Although these results do not rule out the possibility that Fas ligand expression was increased by bisindolylmaleimide VIII, which also would be able to enhance apoptosis of activated T cells, these results support the conclusion that bisindolylmaleimide VIII enhances apoptosis of activated T cells through a Fas-mediated signaling system, thus resulting in the rapid elimination, by an autocrine mechanism, of T cells expressing Fas ligand.

Bisindolylmaleimide VIII prevents autoimmune diseases. Defective or insufficient activation-induced cell death in autoreactive T cells is thought to be an essential factor contributing to the development of some autoimmune diseases after autoantigen challenge. Thus, facilitation of activation-induced cell death during the activation of autoreactive T cells may be an ideal strategy for increasing the elimination of autoreactive T cells, and thus be useful in the treatment of certain autoimmune diseases. To determine whether the administration of bisindolylmaleimide VIII during the activation of autoreactive T cells can prevent the development of autoimmune diseases, two T cell-mediated autoimmune disease models were tested: the Lewis rat model of experimental allergic encephalitis (EAE), and the Lewis adjuvant arthritis model. To induce EAE, Lewis rats were immunized with myelin basic protein (MBP) to activate MBP-reactive T cells. The immunized rats were treated subsequently with 250 μg of bisindolylmaleimide VIII every other day for five doses. All of the control rats (12 of 12) treated with vehicle developed severe clinical symptoms of EAE, but only 33% of the bisindolylmaleimide VIII-treated rats (3 of 9) developed any symptoms of EAE. In the few bisindolylmaleimide VIII-treated rats that developed symptoms of EAE, the onset was slightly delayed and the recovery was twice as rapid as in control rats as shown in Table 2. The EAE in the control rats (12 of 12) was progressive and severe. Most rats developed the manifestations of paralysis (clinical score, 3). In contrast, the 33% of rats that showed any symptoms of EAE with bisindolylmaleimide VIII treatment did not progress to a severe form (clinical score, <2). Thus, treatment with bisindolylmaleimide VIII reduced the incidence of symptoms, delayed the onset of disease, reduced the severity of disease, and enhanced recovery, indicating that bisindolylmaleimide VIII may facilitate apoptosis of MBP-reactive T cells in vivo.

TABLE 2

Effect of bisindolylmaleimide VIII on the development of EAE

| Treatment | Incidence | Onset (days) | Duration (days) | Clinical Score |
| --- | --- | --- | --- | --- |
| Control | 12 of 12 | 12.7 ± 0.9 | 7.0 ± 0.8 | 3.5 ± 0.5 |
| Bis VIII | 3 of 9 | 15.0 ± 0.9 | 3.5 ± 0.4 | 1.7 ± 03 |

Rats were immunized with MPB and injected with bisindolylmaleimide VIII (Bis VIII) or vehicle only (Control) and assessed for paralysis (Clinical Score: the average maximum achieved by each rat that attained a score of 1 or more). Onset, the day each rat achieved a clinical score of 1 or more.

Lewis rat adjuvant arthritis also is a T cell-mediated autoimmune disease, Five doses of bisindolylmaleimide VIII (250 µg per dose) or vehicle were administrated to rats as in the EAE model. Histological analysis showed that 100% of rats (12 of 12) treated with vehicle developed substantial symptoms of arthritis thirty days after immunization as shown in Table 3. Severe inflammation, including cartilage erosion and bone destruction, was observed in most vehicle-treated rats. In contrast, less than 10% of the bisindolylmaleimide VIII-treated rats (1 of 12) had arthritic lesions, and the single positive rat attained a severity score of only 1, compared with an average score of 3 for the vehicle-treated rats. Thus, amelioration of autoimmune symptoms in two different models confirmed that bisindolylmaleimide VIII inhibits the development of T cell-mediated autoimmune disease.

TABLE 3

Effect of bisindolylmaleimide VIII on the development of adjuvant-induced arthritis

| Treatment | Incidence | Severity Score |
| --- | --- | --- |
| Control | 12 of 12 | 2.7 ± 0.6 |
| Bis VIII | 1 of 12 | 1 |

Rats were immunized with Freund's complete adjuvant and injected with bisindolylmaleimide VIII (Bis VIII) or vehicle (Control). Severity of arthritis was evaluated histologically 30 days after immunization; the severity score is given as the average maximum achieved by each rat that attained a score of 1 or more.

Figure 7A:
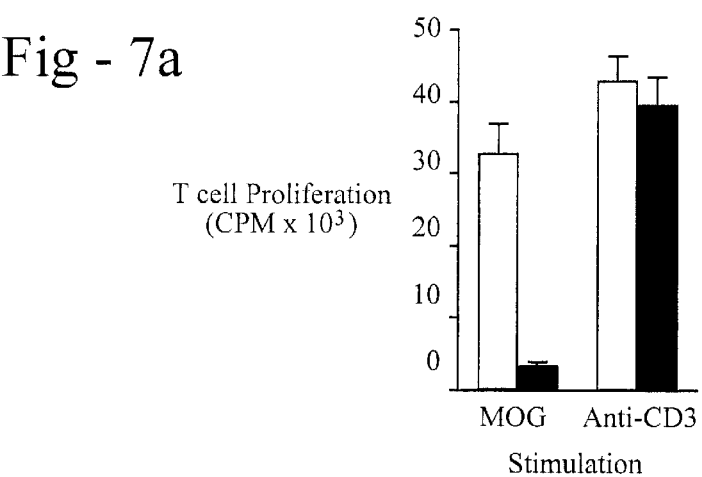
FIGS. 7a–b—Bisindolylmaleimide VIII inhibits antigen-specific T-cell response. C57BL/6–+/+ (a) and –lpr/lpr (b) mice were immunized with the MOG peptide and injected with bisindolylmaleimide VIII on day 3 after immunization; this treatment was repeated every other day for a total of three treatments. At day 10 after immunization, spleen T cells were purified and stimulated with the MOG peptide or anti-CD3 antibody. T-cell proliferative response was determined by the $^3$H-thymidine incorporation assay. Basal proliferation was similar in the lpr/lpr and wild-type T cells in the absence of MOG or anti-CD3. Open bars, control; filled bars, bisindolylmaleimide VIII. Values shown are mean±s.e.m. of five mice.
Figure 7B:
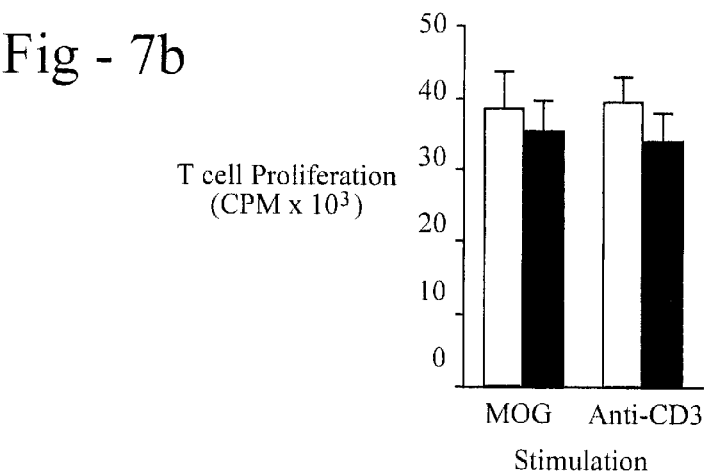

To determine if increased activation-induced cell death in autoreactive T cells caused by bisindolylmaleimide VIII treatment is a chief mechanism contributing to its inhibition of the development of autoimmune disease, the effect of in vivo treatment with bisindolylmaleimide VIII on the autoreactive T-cell response in both wild-type and lpr/lpr mice was examined. C57BL/6 mice were immunized with myelin oligodendrocyte glycoprotein (MOG) peptide 35–55, which induces EAE by generating MOG-specific T cells in this train of mice. Suen et al., *J. Exp. Med* 186, 1233–1240 (1997). Treatment of wild-type B5 mice with bisindolylmaleimide VIII after autoantigen challenge substantially decreased the T-cell response to the subsequent MOG peptide stimulation compared with that of untreated control mice (see FIG. 7a). This inhibited T-cell response is not due to a general immunodeficiency caused by bisindolylmaleimide VIII, as the T-cell response to anti-CD3 stimulation in treated animals was unimpaired (see FIG. 7a). Furthermore, the T-cell response to the MOG peptide or anti-CD3 stimulation in bisindolylmaleimide-treated lpr/lpr mice was not substantially affected by bisindolylmaleimide VIII treatment (see FIG. 7b). These results indicate that enhancement of activation-induced cell death in autoantigen-primed T cells by bisindolylmaleimide VIII is a chief mechanism by which autoantigen-reactive T cells are specifically eliminated.

Deficient or impaired apoptosis can have severe, even lethal, consequences. Thus, with blocked apoptosis, transformed cells can evade elimination during tumor growth, and surviving autoreactive T cells can attack host tissues. Many therapeutic strategies are aimed at initiating apoptosis with exogenous agents, but the dose dependency and cell selectivity of such treatments can limit the degree of target cell elimination. An alternative strategy is to potentiate endogenous apoptotic signaling mechanisms that may be completely blocked or partially impaired in target cells, as may occur in transformed cells or autoreactive T cells. Here, cells resistant to Fas-mediated apoptosis were treated with bisindolylmaleimide VIII, which not only overcame the almost complete block of Fas-mediated apoptosis shown by both human 1321N1 astrocytoma cells and human Molt-4 T cells, but also potentiated weak and moderate apoptotic signals generated by a low dose of anti-Fas antibody in Jurkat and CEM-6 T cells, respectively. The facilitation of Fas-mediated apoptosis by bisindolylmaleimide VIII in autoreactive T cells was remarkably effective in blocking the development of two well-known autoimmune diseases, indicating that this may be a prototypical model for the development of improved therapeutic interventions in certain diseases associated with insufficient apoptotic signaling activity.

Fas-mediated apoptosis can be regulated by the levels of expression of Fas or Fas ligand, but these do not always correlate with cellular vulnerabilities to apoptosis, indicating that intracellular signaling processes associated with Fas-mediated apoptosis can be essential in determining if cells undergo apoptosis after activation of Fas. Su et al., *Immunity* 2, 353–362 (1995); Miyawaki et al., *J. Immunol.* 149, 3753–3758 (1992). Bisindolylmaleimide VIII seems to facilitate intracellular signaling initiated by activation of Fas, and this facilitation occurred in cells with a wide range of sensitivities to Fas-mediated apoptosis. Like most apoptotic processes, the Fas apoptosis signaling pathway is complex and has not been fully defined, so the sites affected by bisindolylmaleimide VIII remain to be identified. Although the bisindolylmaleimides have traditionally been considered selective inhibitors of PKC (Toullec et al., *J. Biol. Chem.*, 266, 1571–1581 (1991); Bit et al., *J. Med. Chem.* 36, 21–29 (1993); Jacobson et al., *J. Pharmacol. Exp. Therap.* 275, 995–1002 (1995)), this does not seem to be the action accounting for facilitation of Fas-mediated apoptosis, as not all bisindolylmaleimide derivatives that inhibit PKC inhibitors had no effect. One possibility is that facilitation of Fas-mediated apoptosis by the bisindolylmaleimides occurs through inhibition of kinases other than PKC, which is consistent with previous reports that protein dephosphorylation, such as that mediated by hematopoietic cell protein tyrosine phosphatase, plays a part in the Fas apoptosis signaling pathway. Su et al., *Immunity* 2, 353–362 (1995). The main derivative studied here, bisindolylmaleimide VIII, modulates the activities of a variety of enzymes, such as mitogen-activated protein kinase phosphatase-1, Jun N-terminal kinase and tyrosine kinase signaling. Beltman et al., *J. Biol. Chem.* 271, 27018–27024 (1996); Alessi et al., *FEBS Lett.* 402, 121–123 (1997); Yeo et al., *Biochim. Biophys. Acta,* 1356, 308–320 (1997). Thus, several candidate sites for the potentiating effect of bisindolylmaleimide VIII require investigation.

The interaction of bisindolylmaleimide VIII with Fas-mediated apoptosis was investigated in T cells as well as astrocytoma cells to address the cell selectivity of this interaction and because animal models of autoimmune diseases associated with impaired elimination of autoreactive T cells are well-described and are amenable to testing potential in vivo therapeutic interventions. A step towards in vivo use was the finding that bisindolylmaleimide VIII did not have a substantial effect on activated T cells from Fas-deficient lpr/lpr mice, supporting the conclusion that the interaction is dependent on signaling through Fas. Moreover, bisindolylmaleimide VIII selectively promoted apoptosis in activated T cells, while having little effect on non-activated T cells. Because bisindolylmaleimides only promote Fas-mediated apoptosis in those T cells activated by autoantigens, it overcomes the disadvantage of non-specific immunosuppression. This raised the possibility that bisindolylmaleimide VIII may be especially useful for eliminating activated T cells that contribute to autoimmune diseases.

The finding that defective expression of Fas and Fas ligand causes the development of autoimmune diseases in lpr/lpr mice and gld/gld mice, respectively (Watanabe-Fukunaga et al., *Nature* 356, 314–317 (1992); Takahashi et al., *Cell* 76, 969–976 (1994)), indicates that insufficient Fas-mediated apoptosis may lead to loss of T-cell tolerance and hence to the development of autoimmune disease. Therefore, elimination of autoreactive T cells has been a therapeutic strategy for the treatment of autoimmune diseases. Enhancement of activation-induced cell death by the administration of high doses of autoantigens has been shown to effectively deplete autoreactive T cells and to abrogate the clinical and pathological symptoms of autoimmune encephalomyelitis. McFarland et al., *Adv. Exp. Med. Biol.* 383, 157–166 (1995); Tabi et al., *Int. Immunol.* 7, 967–973 (1995). As an alternative strategy, amelioration of autoimmune diseases may be attained by facilitation of Fas-mediated apoptosis in activated T cells, as was attained here by the administration of bisindolylmaleimide VIII in two animal models. In both the Lewis rat model of EAE and the Lewis adjuvant arthritis model, 100% of the vehicle-treated rats showed severe symptoms. In contrast, most of the rats treated with bisindolylmaleimide VIII showed no symptoms, and those rats with symptoms had greatly decreased severity of symptoms compared with those of vehicle-treated rats. These results demonstrate the feasibility of treatment of T cell-mediated autoimmune diseases by agents that facilitate Fas-mediated apoptosis of activated autoreactive T cells. Thus, these experiments indicate that agents that overcome blocked apoptotic signaling processes may be useful therapeutically, and, specifically, that bisindolylmaleimides might be potential leading compounds useful in treating T cell-mediated autoimmune diseases in humans.

Identification of a Non-Apoptotic Fas-Linked Signaling Cascade Increasing bcl-2 Levels Through Activation of Nitric Oxide Synthase Fas, also called CD95 or APO-1, is a member of the death domain-containing tumor necrosis factor (TNF) receptor family. Activation of Fas by Fas ligand or by an agonistic anti-Fas antibody can trigger intracellular signaling cascades leading to apoptosis. Upon Fas activation, two initial steps have been described which activate complementary cascades contributing to cell death, involving recruitment of cellular proteins, called FADD and Daxx, to bind independent sites on the intracellular domain of Fas. FADD is an adaptor protein that recruits procaspase-8 leading to its activation and the subsequent activation of a caspase cascade. Daxx activates the kinase ASK1 which leads to the activation of the Jun N-terminal kinase (JNK) and p38 MAP kinase pathways, although the contribution of this cascade to Fas-mediated apoptosis is not fully elucidated (Chang et al., *Proc. Natl. Acad. Sci USA* 96, 1252–1256 (1990)).

An hitherto unknown signaling cascade initiated by activation of Fas is described which does not lead to apoptosis. To identify this signaling cascade, advantage was taken of the recently described properties of human astrocytoma 1321N1 cells. Fas is expressed in 1321N1 cells, but activation of Fas in these cells fails to trigger apoptosis unless facilitory bisindolylmaleimides are provided which convert the cells from non-apoptotic responders to Fas activation, to cells that efficiently apoptose (Zhou et al., *Nature Medicine* 5, 42–48 (1999)). Thus, it was hypothesized that these cells could be used to differentiate signaling cascades emanating from Fas that are independent of apoptosis from those that lead to apoptosis. Additionally, the sites in the Fas-linked signaling cascades that are affected by bisindolylmaleimide which could account for its ability to facilitate Fas-induced apoptosis were investigated.

Members of the bcl-2 protein family have critical regulatory roles in apoptosis. Apoptosis generated by many mechanisms is counteracted by the anti-apoptotic protein bcl-2, but mechanisms that regulate cellular bcl-2 levels remain poorly defined. This study tested if activation of Fas modulated bcl-2 levels in cells not susceptible to Fas-induced apoptosis.

Figure 8A:
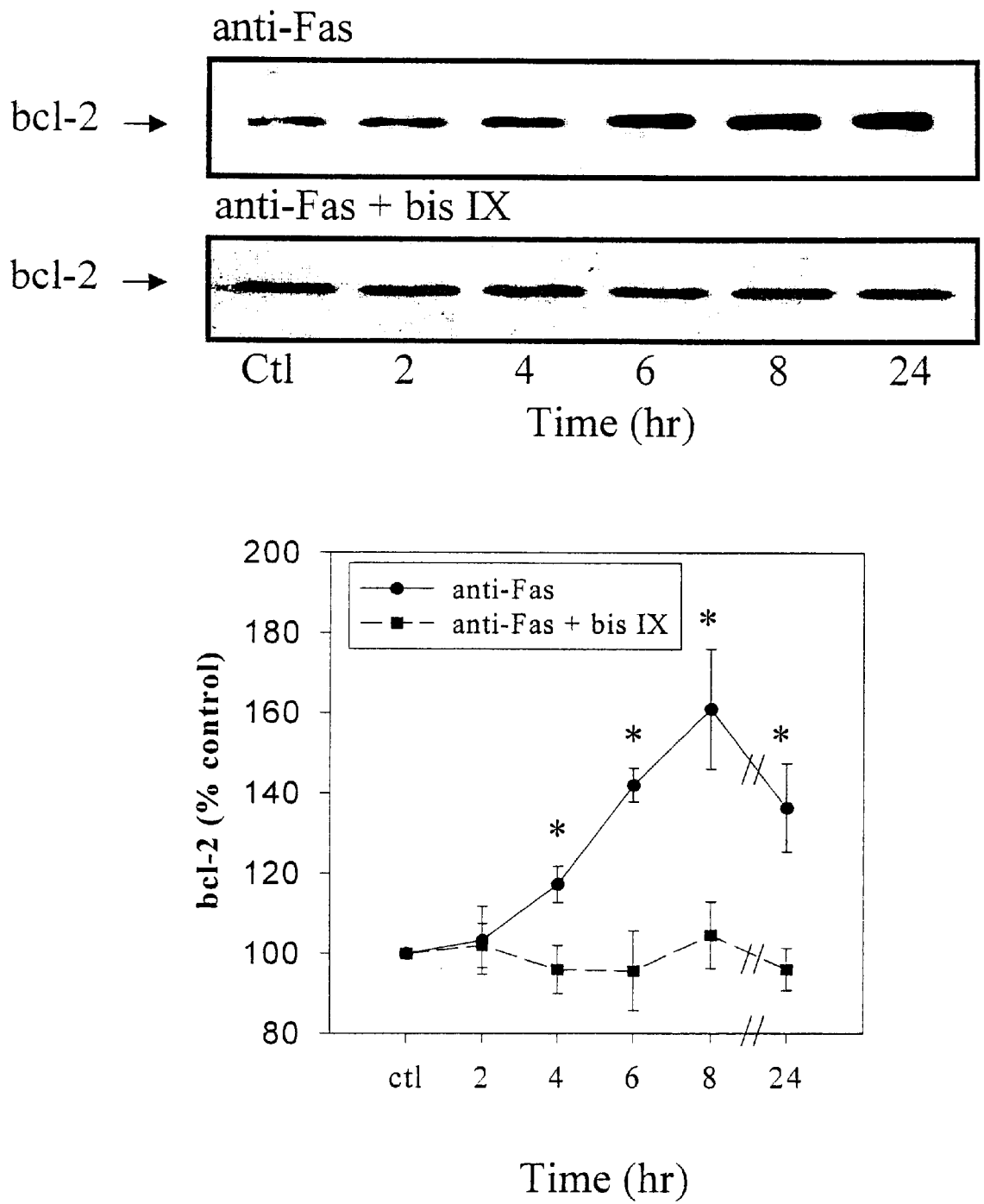
FIGS. 8a–c—Fas activation increases bcl-2 levels in 1321N1 cells. (A) Representative immunoblots and quantitative values of bcl-2 in cells harvested two, four, six, eight, and twenty-four hours after treatment with agonistic anti-Fas antibody alone or with 2.5 µM bisindolylmaleimide IX. Bcl-2 levels were significantly increased ($p<0.05$) after treatment with anti-Fas alone but not after coadministration of bisindolylmaleimide IX. (B) Representative immunoblot and quantitative values of bcl-2 in cells eight hours after treatment with anti-Fas alone or with coadministration if bisindolylmaleimides I, II, IV, VIII, or IX. Only bisindolylmaleimides VIII and XI blocked anti-Fas-induced increases in bcl-2. (C) Representative immunoblots of bax, bcl-x, and bad in cells harvested four or eight hours after treatment with anti-Fas. No significant changes were observed.
Figure 8B:
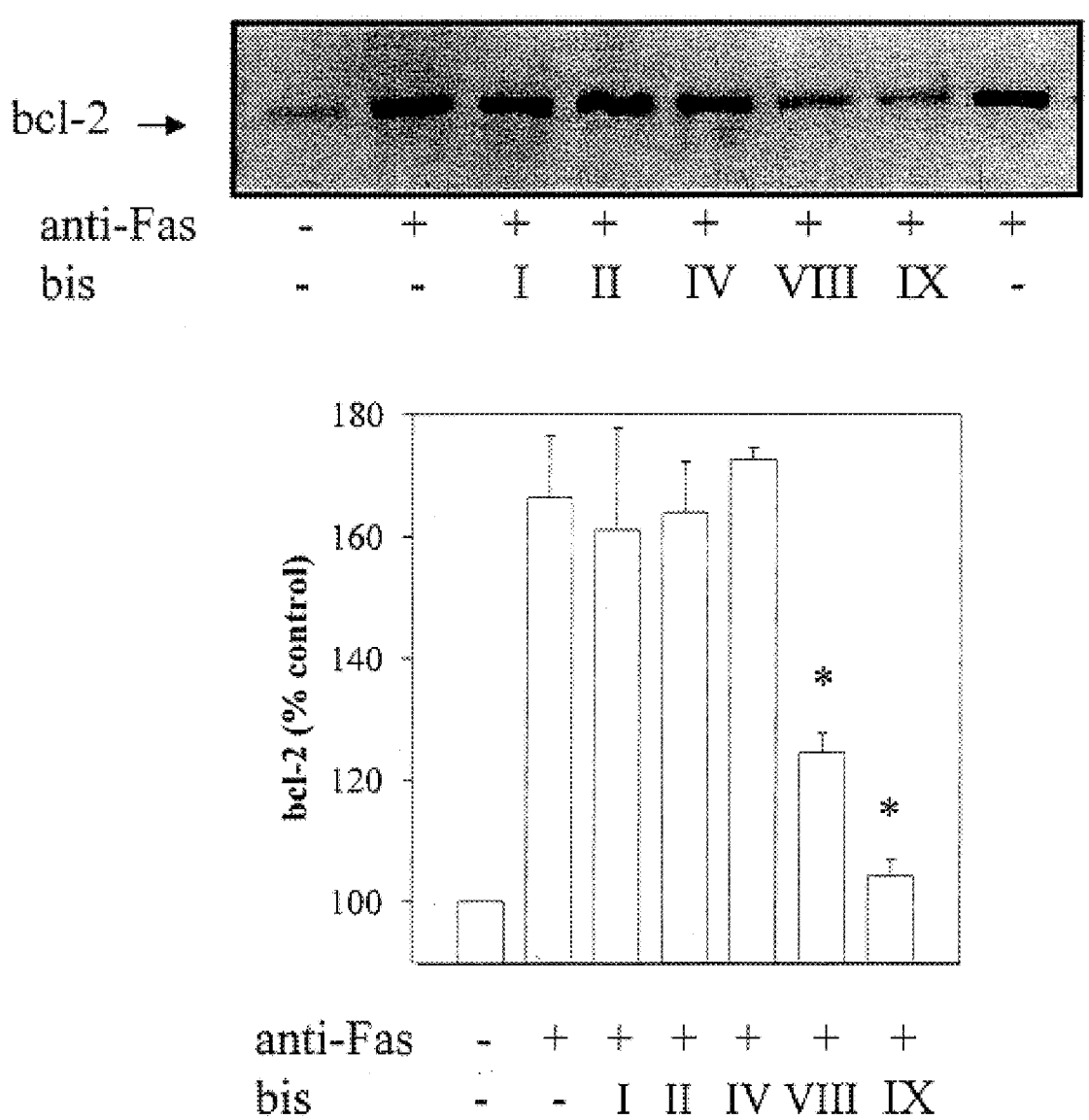
Figure 8C:
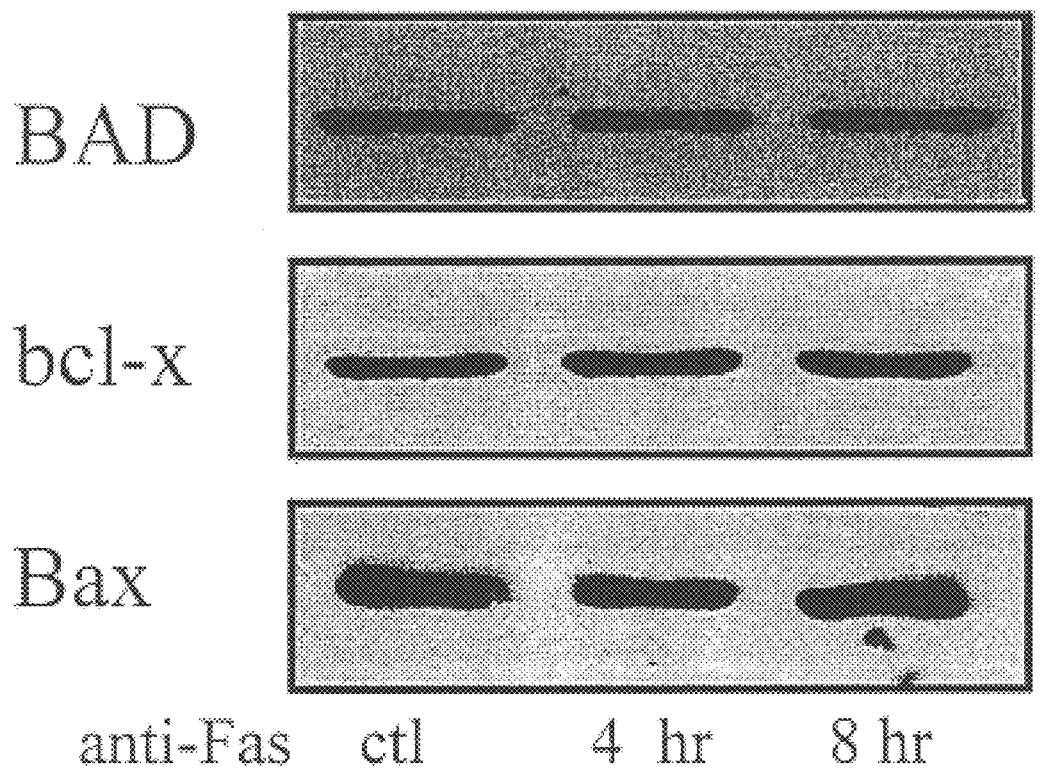

Activation of Fas in 1321N1 cells did not induce apoptosis but caused a time-dependent increase in the levels of bcl-2 (FIG. 8A). In contrast, facilitation of Fas-induced apoptosis by coadministration of 2.5 $\mu$M bisindolylmaleimide IX left the bcl-2 level unchanged from that in untreated cells. Bisindolylmaleimides VIII and IX facilitate Fas-induced apoptosis in 1321N1 cells, whereas bisindolylmaleimide I, II, and IV do not (Zhou et al., *Nature Medicine* 5, 42–48 (1999)). These distinctions were also evident in the bisindolylmaleimide derivative's capabilities to modulate Fas-induced increases in bcl-2, as bisindolylmaleimide VIII and IX (which facilitate apoptosis) inhibited Fas-induced increases in bcl-2, but bisindolylmaleimide I, II, and IV did not (FIG. 8B). In contrast to bcl-2, activation of Fas did not alter the levels of several other members of the bcl-2 family, including Bax, BAD, and bcl-x (FIG. 8C). These results indicated that Fas activation initiates a signaling cascade leading to increased levels of bcl-2 in cells not undergoing apoptosis which appears to be distinct from the previously described signaling cascades that lead to apoptosis.

To verify that signaling leading to increased bcl-2 levels was independent of the FADD and Daxx-dependent pathways, the activation state of each of these was examined in Fas-activated 1321N1 cells in the absence and presence of 2.5 $\mu$M bisindolylmaleimide. The first known step in the Fas-induced apoptosis signaling cascade involves recruitment of FADD to the intracellular death domain of Fas. This response was examined by measuring the translocation of FADD from the cytosol to the membrane and the coimmunoprecipitation of FADD with Fas after activation with an agonistic anti-Fas in the absence or presence of bisindolylmaleimide. In untreated cells, little FADD was detected in membrane fractions, and there was little change after treating cells individually with bisindolylmaleimide or agonistic anti-Fas alone (FIG. 9A). However, coadministration of bisindolylmaleimide with anti-Fas, which initiates apoptosis, produced a large increase in membrane-associated FADD. Similarly, coadministration of bisindolylmaleimide and anti-Fas caused a large increase in the coprecipitation of FADD with Fas (FIG. 9B), whereas treatment with either bisindolylmaleimide or anti-Fas alone did not. These results indicate that in 1321N1 cells the FADD-mediated apoptotic cascade is not initiated by activation of Fas unless bisindolylmaleimide is also administered, in agreement with previous measurements of apoptosis in these cells (Zhou et al., *Nature Medicine* 5, 42–48 (1999)).

Figure 10:
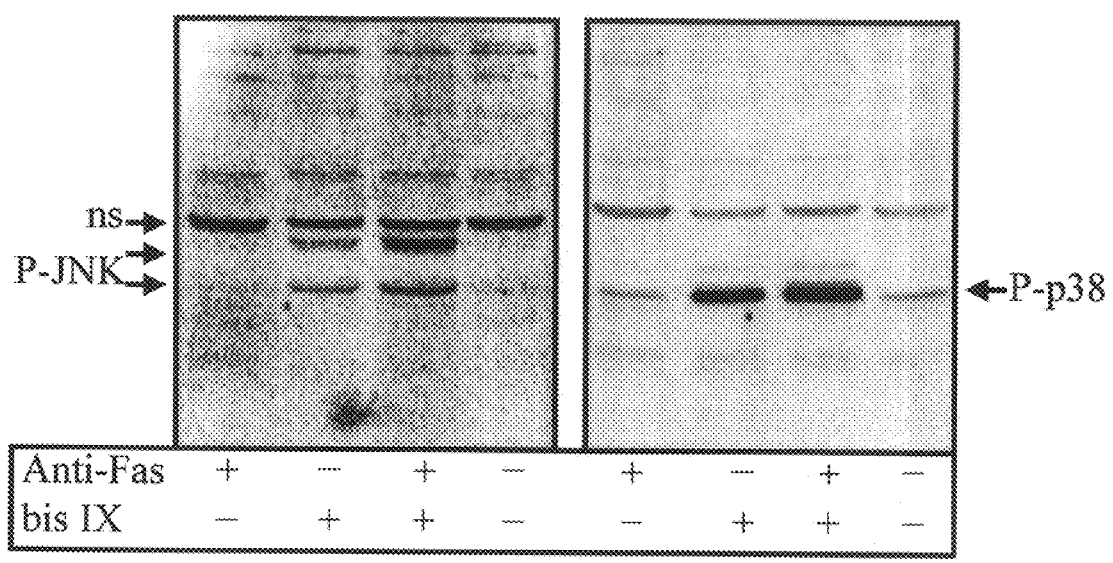
FIG. 10—Activation of p38 and JNK. Representative immunoblots of tyrosine phosphorylated p38 and JNK obtained from cells treated with anti-Fas, bisindolylmaleimide IX, or both agents. Treatment with anti-Fas alone caused no changes, but increases were caused by treatment with bisindolylmaleimide IX and these were increased further by coadministration of anti-Fas.

The other previously described Fas-mediated signaling cascade involves Daxx recruitment and the subsequent activation of p38 and JNK. The activation state of these kinases was measured by assessing the phosphotyrosine immunoreactivity of the kinases, which increases in conjunction with kinase activation. Activation of Fas in 1321N1 cells did not activate either kinase unless bisindolylmaleimide was also administered, in which case there were large increases in the phosphotyrosine immunoreactivities of both p38 and JNK (FIG. 10). It is of interest to note that treatment with bisindolylmaleimide alone also increased the tyrosine immunoreactivities of p38 and JNK, which were increased further upon activation of Fas. This is in accord with a recent report that 10 µM bisindolylmaleimide activated JNK and p38 in Rat-1 fibroblasts (Beltman et al., *J. Biol. Chem* 274, 3772–3780 (1999)). Thus, neither the FADD nor the Daxx signaling pathways were activated by treatment of 1321N1 cells with an agonistic anti-Fas antibody alone, but coadministration of bisindolylmaleimide facilitated each of these signaling cascades, as well as facilitating Fas-induced apoptosis.

Figure 11:
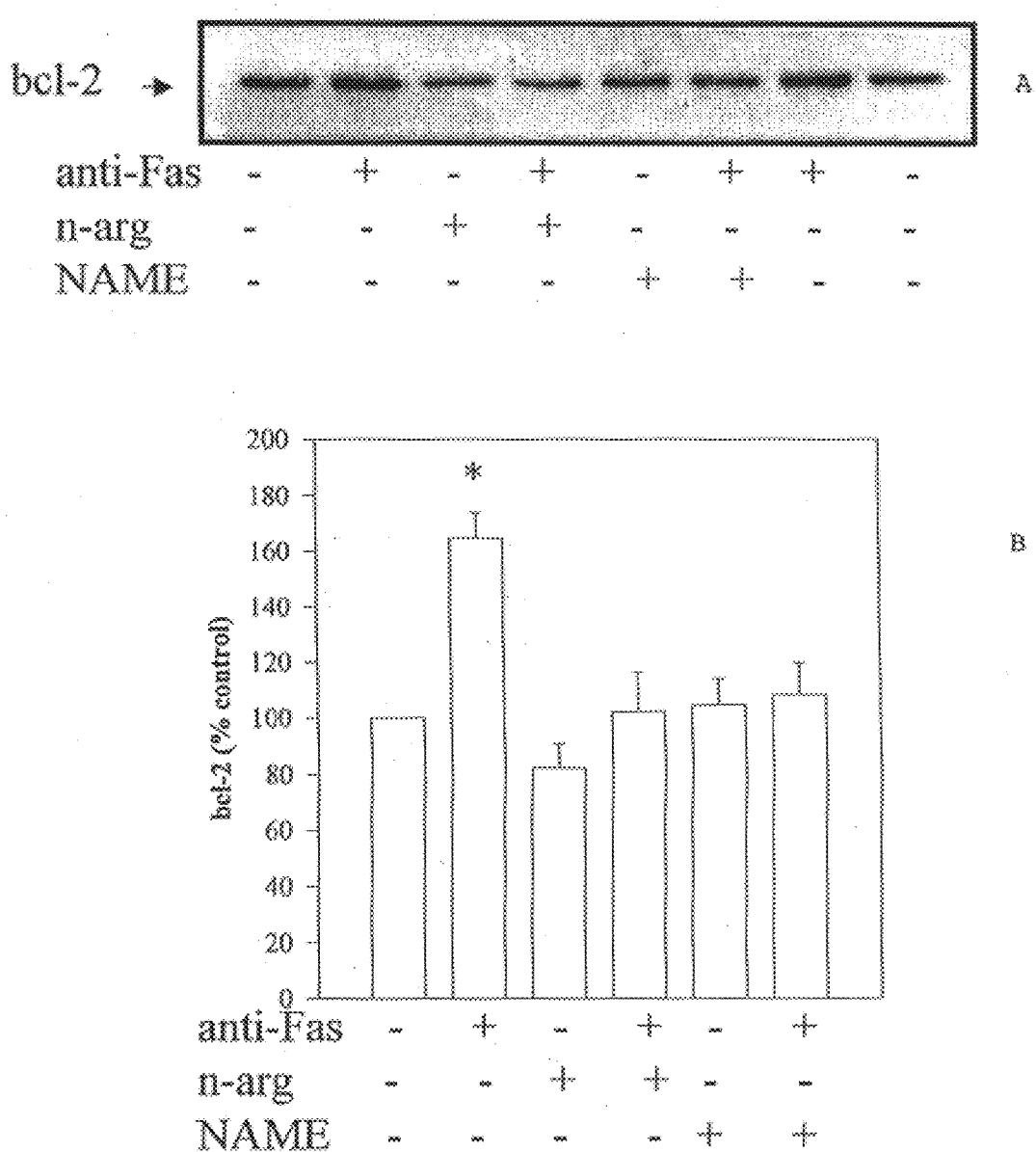
FIG. 11—Nitric oxide (NO) mediates Fas-induced increases in bcl-2. (A) Representative immunoblots and (B) quantitative values of bcl-2 in 1321N1 cell lysates prepared after treatment with anti-Fas alone or after preincubation with the nitric oxide synthase inhibitors NAME or nitroarginine. Each nitric oxide inhibitor blocked Fas-induced increases in bcl-2.

The results described above clearly demonstrate that neither the FADD nor the Daxx signaling cascades is activated by application of an agonistic anti-Fas antibody to 1321N1 cells, but a signaling cascade leading to increased levels of bcl-2 is activated by this treatment. Conversely, facilitation of the FADD and Daxx pathways by administrating bisindolylmaleimide with Fas activation abrogated the signal leading to bcl-2. Because a recent report indicated that nitric oxide (NO) is able to increase bcl-2 levels (Suschek et al., *J. Biol. Chem.* 274, 6130–6137 (1999)), we tested if NO mediated Fas-induced increases in bcl-2. Pretreatment with either of the NO synthase inhibitors NAME or nitro-arginine blocked the increases in bcl-2 levels caused by activation of Fas (FIG. 11). These results indicate that NO is necessary for Fas-induced increases in bcl-2 and raised the possibility that Fas activation leads to the stimulation of NO production.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for inducing apoptosis in a target cell of a subject, said method comprising administering to the subject a pharmaceutically effective amount of at least one compound of the formula:

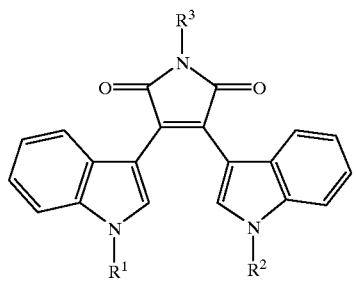

I wherein:
$R^1$ is hydrogen, $C_1$–$C_{12}$ alkyl, $C_1$–$C_{12}$ substituted alkyl, $C_3$–$C_7$ heterocycle, or $C_3$–$C_7$ substituted heterocycle;
$R^2$ and $R^3$ are independently H or $C_1$–$C_{12}$ alkyl; and the pharmaceutically acceptable salts, esters, amides, and prodrugs thereof, wherein following said administering step, the target cell is caused to undergo apoptosis, wherein the target cell has impaired apoptosis.

2. A method according to claim 1, wherein $R^1$ is $C_1$–$C_{12}$ substituted alkyl.

3. A method according to claim 1, wherein $R^1$ is $C_1$–$C_{12}$ substituted alkyl, $R^2$ is methyl, and $R^3$ is hydrogen.

4. A method according to claim 1, wherein the compound is selected from a group consisting of:

2-[1-(3-Aminopropyl)-indol-3-yl]-3-(indol-3-yl)maleimide;
2,3-bis(1H-indol-3-yl)-N-methylmaleimide;
2-[1-(2-Piperidin-2-yl)ethyl]-1H-indol-3-yl]-3-(1H-indol-3yl)maleimide;
2-[1-(3-Piperazinopropyl)-1H-indol-3-yl]-3-(1H-indol-3-yl)maleimide;
2-[1-(3-Aminopropyl)indol-3-yl]-3-(1-methylindol-3-yl)maleimide;
2-[1-[3-(Amidinothio)propyl]-1H-indol-3-yl-]-3-(1-methylindol-3-yl)maleimide;
2-[8-Aminomethyl]-6,7,8,9-tetrahydropyrido[1,2-a]indol-3-yl]-3-(1-methylindol-3-yl)maleimide;
2-(8-Dimethylamino)methyl)-6,7,8,9-tetrahydropyrido[1,2-a]indol-3-yl)-3-(1-methylindol-3-yl)maleimide; and
the pharmaceutically acceptable salts, esters, amides, and prodrugs thereof.

5. A method according to claim 1, wherein the target cell is neoplastic.

6. A kit for the administration of bisindolylmaleimide compounds comprising at least one bisindolylmaleimide compound of Formula I of claim 1.

7. A kit according to claim 6 further comprising an administering device.

8. A method for inducing apoptosis in a target cell of a subject, said method comprising administering to the subject a pharmaceutically effective amount of at least one compound of the formula:

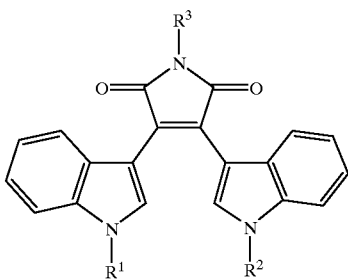

wherein:

R¹ is hydrogen, $C_1$–$C_{12}$ alkyl, $C_1$–$C_{12}$ substituted alkyl, $C_3$–$C_7$ heterocycle, or $C_3$–$C_7$ substituted heterocycle;

R² and R³ are independently H or $C_1$–$C_{12}$ alkyl; and the pharmaceutically acceptable salts, esters, amides, and prodrugs thereof, wherein following said administering step, the target cell is caused to undergo apoptosis, wherein R¹ is $C_3$–$C_7$-heterocycle.

9. A method according to claim 8, wherein R¹ is $C_3$–$C_7$-substituted heterocycle.

10. A method according to claim 8, wherein R¹ is $C_3$–$C_7$ substituted heterocycle, R² is methyl, and R³ is hydrogen.

11. A method for inducing apoptosis in a target cell of a subject, said method comprising administering to the subject a pharmaceutically effective amount of at least one compound of the formula:

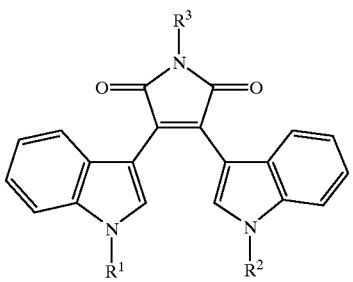

wherein:

R¹ is hydrogen, $C_1$–$C_{12}$ alkyl, $C_1$–$C_{12}$ substituted alkyl, $C_3$–$C_7$ heterocycle, or $C_3$–$C_7$ substituted heterocycle;

R² and R³ are independently H or $C_1$–$C_{12}$ alkyl; and the pharmaceutically acceptable salts, esters, amides, and prodrugs thereof, wherein following said administering step, the target cell is caused to undergo apoptosis, wherein the target cell is a lymphocyte.

12. A method according to claim 11, wherein the lymphocyte is a T cell.

13. A method according to claim 12, wherein the T cell is activated.

14. A method for treating a subject having a T cell mediated autoimmune disorder, said method comprising administering to a subject having a T cell mediated autoimmune disorder characterized by defective or insufficient activation-induced cell death of activated autoreactive T cells, a pharmaceutically effective amount of at least one compound of the formula:

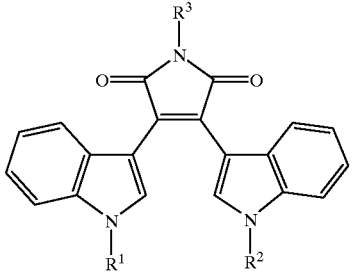

wherein:

R¹ is hydrogen, $C_1$–$C_{12}$ alkyl, $C_1$–$C_{12}$ substituted alkyl, $C_3$–$C_7$ heterocycle, or —$C_3$–$C_7$ substituted heterocycle;

R² and R³ are independently H or $C_1$–$C_{12}$ alkyl; and the pharmaceutically acceptable salts, esters, amides, and prodrugs thereof, wherein administration of the at least one compound of formula I causes activation-induced cell death of the activated autoreactive T cells.

15. A method according to claim 14 further comprising the step of inducing apoptosis in the activated T cells.

16. A method according to claim 14, wherein R¹ is $C_1$–$C_{12}$ substituted alkyl.

17. A method according to claim 14, wherein R¹ is $C_3$–$C_7$-heterocycle.

18. A method according to claim 14, wherein R¹ is $C_3$–$C_7$-substituted heterocycle.

19. A method according to claim 14, wherein R¹ is $C_1$–$C_{12}$ substituted alkyl, R² is methyl, and R³ is hydrogen.

20. A method according to claim 14, wherein R¹ is $C_3$–$C_7$ substituted heterocycle, R² is methyl, and R³ is hydrogen.

21. A method according to claim 14, wherein the compound is:

2-[1-(3-Aminopropyl)-indol-3-yl]-3-(indol-3-yl)maleimide;
2,3-bis(1H-indol-3-yl)-N-methylmaleimide;
2-[1-(2-Piperidin-2-yl)ethyl]-1H-indol-3-yl]-3-(1H-indol-3yl)maleimide;
2- [1-(3-Piperazinopropyl)-1H-indol-3-yl]-3-(1H-indol-3-yl)maleimide;
2-[1-(3-Aminopropyl)indol-3-yl]-3-(1-methylindol-3-yl) maleimide;
2-[1-[3-(Amidinothio)propyl]-1H-indol-3-yl-]-3-(1-methylindol-3-yl)maleimide;
2-[8-Aminomethyl]-6,7,8,9-tetrahydropyrido[1,2-a]indol-3-yl]-3-(1-methylindol-3-yl)maleimide;
2-(8-Dimethylamino)methyl]-6,7,8,9-tetrahydropyrido[1,2-a]indol-3-yl)-3-(1-methylindol-3-yl)maleimide; and the pharmaceutically acceptable salts, esters, amides, and prodrugs thereof.

22. A method for preventing T cell tolerance in a subject, said method comprising eliminating activated T cells having impaired apoptosis by administering a pharmaceutically effective amount of at least one compound of the formula:

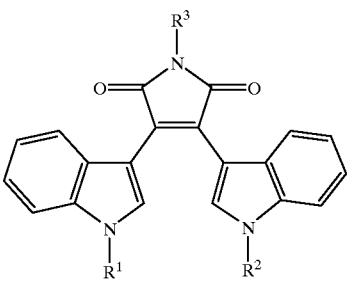

wherein:
  $R^1$ is hydrogen, $C_1$–$C_{12}$ alkyl, $C_1$–$C_{12}$ substituted alkyl, $C_3$–$C_7$ heterocycle, or $C_3$–$C_7$ substituted heterocycle;
  $R^2$ and $R^3$ are independently H or $C_1$–$C_{12}$ alkyl; and the pharmaceutically acceptable salts, esters, amides, and prodrugs thereof, wherein following said administering step, the activated T cells having impaired apoptosis are caused to undergo apoptosis.

23. A method for facilitating Fas-mediated intracellular signaling in a cell, said method comprising administering to the cell a pharmaceutically effective amount of at least one compound of a formula:

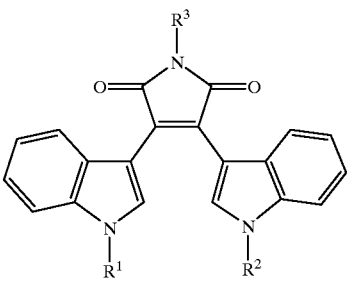

wherein:
  $R^1$ is hydrogen, $C_1$–$C_{12}$ alkyl, $C_1$–$C_{12}$ substituted alkyl, $C_3$–$C_7$ heterocycle, or —$C_3$–$C_7$ substituted heterocycle;
  $R^2$ and $R^3$ are independently H or $C_1$–$C_{12}$ alkyl; and the pharmaceutically acceptable salts, esters, amides, and prodrugs thereof.

24. A method for inhibiting Fas-induced production of bcl-2 anti-apoptotic protein, said method comprising administering to the subject a pharmaceutically effective amount of at least one compound of the formula:

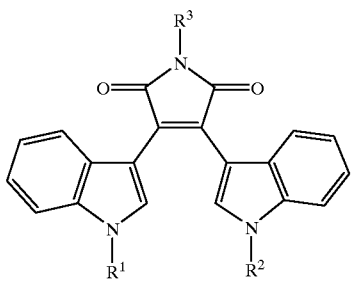

wherein:
  $R^1$ is hydrogen, $C_1$–$C_{12}$ alkyl, $C_1$–$C_{12}$ substituted alkyl, $C_3$–$C_7$ heterocycle, or $C_3$–$C_7$ substituted heterocycle;
  $R^2$ and $R^3$ are independently H or $C_1$–$C_{12}$ alkyl; and the pharmaceutically acceptable salts, esters, amides, and prodrugs thereof.

25. A method according to claim 24, wherein $R^1$ is $C_1$–$C_{12}$ substituted alkyl.

26. A method according to claim 24, wherein $R^1$ is $C_3$–$C_7$-heterocycle.

27. A method according to claim 24, wherein $R^1$ is $C_3$–$C_7$-substituted heterocycle.

28. A method according to claim 24, wherein $R^1$ is $C_1$–$C_{12}$ substituted alkyl, $R^2$ is methyl, and $R^3$ is hydrogen.

29. A method according to claim 24, wherein $R^1$ is $C_3$–$C_7$ substituted heterocycle, $R^2$ is methyl, and $R^3$ is hydrogen.

30. A method according to claim 24, wherein the compound is:

2-[1-(3-Aminopropyl)-indol-3-yl]-3-(indol-3-yl)maleimide;
2,3-bis(1H-indol-3-yl)-N-methylmaleimide;
2-[1-(2-Piperidin-2-yl)ethyl]-1H-indol-3-yl]-3-(1H-indol-3yl)maleimide;
2-[1-(3-Piperazinopropyl)-1H-indol-3-yl]-3-(H-indol-3-yl)maleimide;
2-[1-(3-Aminopropyl)indol-3-yl]-3-(1-methylindol-3-yl)maleimide;
2-[1-[3-(Amidinothio)propyl]-1H-indol-3-yl-]-3-(1-methylindol-3-yl)maleimide;
2-[8-Aminomethyl]-6,7,8,9-tetrahydropyrido[1,2-a]indol-3-yl]-3-(1-methylindol-3-yl)maleimide;
2-(8-Dimethylamino)methyl)-6,7,8,9-tetrahydropyrido[1,2-a]indol-3-yl)-3-(1-methylindol-3-yl)maleimide, and
the pharmaceutically acceptable salts, esters, amides, and prodrugs thereof.

* * * * *